United States Patent
Tyvoll et al.

(10) Patent No.: US 11,230,787 B2
(45) Date of Patent: Jan. 25, 2022

(54) METAL OXIDE NANOSTRUCTURED SURFACES

(71) Applicant: Alfred E. Mann Institute for Biomedical Engineering at the University of Southern California, Los Angeles, CA (US)

(72) Inventors: David Alvin Tyvoll, San Diego, CA (US); Nan Chen, Temple City, CA (US); Bharat Kumar Menon, Los Angeles, CA (US); Heather Michelle Grandin, San Diego, CA (US); Cesar Escobar Blanco, Los Angeles, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 79 days.

(21) Appl. No.: 16/648,429

(22) PCT Filed: Sep. 21, 2018

(86) PCT No.: PCT/US2018/052291
§ 371 (c)(1),
(2) Date: Mar. 18, 2020

(87) PCT Pub. No.: WO2019/060777
PCT Pub. Date: Mar. 28, 2019

(65) Prior Publication Data
US 2020/0240034 A1    Jul. 30, 2020

Related U.S. Application Data

(60) Provisional application No. 62/562,873, filed on Sep. 25, 2017.

(51) Int. Cl.
| | | |
|---|---|---|
| C25D 11/26 | (2006.01) |
| C25D 11/34 | (2006.01) |
| B82Y 30/00 | (2011.01) |
| B82Y 40/00 | (2011.01) |

(52) U.S. Cl.
CPC .............. C25D 11/26 (2013.01); C25D 11/34 (2013.01); B82Y 30/00 (2013.01); B82Y 40/00 (2013.01)

(58) Field of Classification Search
None
See application file for complete search history.

(56) References Cited

U.S. PATENT DOCUMENTS

| 5,382,347 A | 1/1995 | Yahalom |
| 2011/0125263 A1 | 5/2011 | Webster et al. |

(Continued)

FOREIGN PATENT DOCUMENTS

EP    1 930 480 A1    6/2008

OTHER PUBLICATIONS

International Search Report and Written Opinion dated Apr. 30, 2019, received in International Patent Application No. PCT/US2018/052291.

(Continued)

*Primary Examiner* — Wojciech Haske
(74) *Attorney, Agent, or Firm* — Knobbe, Martens, Olson & Bear LLP

(57) ABSTRACT

Embodiments of nanostructures comprising metal oxide and methods for forming the nanostructure on surfaces are disclosed. In certain embodiments, the nanostructures can be formed on a substrate made of a nickel titanium alloy, resulting in a nanostructure containing both titanium oxide and nickel oxide. The nanostructure can include a lattice layer disposed on top of a nanotube layer. The distal surface of the lattice layer can have a titanium oxide to nickel oxide (Continued)

ratio of greater than 10:1, or about 17:1, resulting in a nanostructure that promotes human endothelial cell migration and proliferation at the interface between the lattice layer and human cells or tissue. The nanostructure may be formed on the outer surface of an implantable medical device, such a stent or an orthopedic implant (e.g. knee implant, bone screw, or bone staple).

14 Claims, 25 Drawing Sheets

(56) References Cited

U.S. PATENT DOCUMENTS

| | | | |
|---|---|---|---|
| 2013/0196128 A1* | 8/2013 | Friedrich | C25D 7/00 428/209 |
| 2013/0341195 A1* | 12/2013 | Shankar | B82Y 30/00 205/50 |
| 2017/0197015 A1 | 7/2017 | Desai et al. | |

OTHER PUBLICATIONS

Invitation to Pay Additional Fees dated Mar. 8, 2019, received in International Patent Application No. PCT/US2018/052291.

Wu et al., "Honeycombed TiO2 Nanotube Arrays with Top-Porous/Bottom-Tubular Structures for Enhanced Photocatalytic Activity," Ceramics International, Mar. 1, 2015, pp. 2527-2532, vol. 41, No. 2.

* cited by examiner

710

Provide a nickel titanium anode and at least one cathode

720

Place anode and cathode(s) into electrical contact through first electrolyte solution containing ethylene glycol, ammonium fluoride, and water

730

Apply about 25V across anode and cathode(s) for about 5 minutes

740

Add hydroiodic acid to first electrolyte solution resulting in second electrolyte solution

750

Apply about 25V across anode and cathode(s) for about 5 minutes

FIG. 11

METAL OXIDE NANOSTRUCTURED SURFACES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD

Embodiments of the present invention relate to nanostructures including metal oxide and methods of making and using the same.

BACKGROUND

Surface modifications have been explored to provide beneficial characteristics to a variety of devices. One of the methods that has been explored for preparing such surface modifications is electrochemical anodization. In electrochemical anodization, the surface being modified forms an anode electrode. The anode is generally then placed into electrical contact with at least one cathode through an electrolyte solution. A voltage is then applied across the anode and cathode for a period of time. Anodization often results in undesirable and uncontrollable amorphous material accumulating on the surface of the anode. Moreover, the resulting material may contain too high of a concentration of cytotoxic elements, such as nickel, rendering the resulting surface unusable for many potential applications. Accordingly, there is a need for reliable methods of preparing surface modifications with desirable structures and elemental compositions.

SUMMARY

The present invention relates to nanostructures comprising metal oxide and methods of forming the same on the surface of substrates. The substrates may be titanium or any titanium alloy, such as a nickel titanium alloy. The metal oxide nanostructures may have a lattice layer disposed on top of a nanotube layer disposed on top of the surface of a substrate. The lattice and nanotube layers may be formed during an anodization process. The distal surface of the lattice layer may or may not be enriched in titanium. Some embodiments of the present metal oxide nanostructures and methods of forming the nanostructures on surfaces have several features, no single one of which is solely responsible for their desirable attributes.

While some embodiments of the resulting metal oxide nanostructured surfaces provide numerous advantages over other known metal oxide layers, they may be particularly beneficial when used with implantable medical devices because they may promote healing by enhancing the integration of the medical device with the surrounding biological tissue. An example is the promotion of endothelial cell migration and proliferation and the inhibition of smooth muscle cell migration and proliferation in the cardiovascular and systemic vascular systems. With a medical device such as a stent, for example, some embodiments may promote the growth of a confluent endothelial layer while inhibiting the growth of the neointima, thus reducing restenosis and leading to long-term patency at the site of implantation. The medical device can also be an orthopedic implant, such as a knee implant, bone screw, or bone staple, such as those used for hand and foot bone fragments osteotomy fixation and joint arthrodesis.

In one embodiment, the nanostructure comprises two layers: a first layer of tubular structures, and a second layer comprising a lattice. The nanostructure can be arranged such that the first layer is situated between a substrate (e.g., a metal article) and the second layer. The substrate can be any suitable metal article, including an implantable medical device such as a stent. In some embodiments, the surface of the metal article comprises a titanium alloy, such as a nickel titanium alloy. The first layer can be formed at least in part from the surface of the substrate via anodization. The tubular structures comprise metal oxide(s). The tubular structures may or may not further comprise carbon, fluoride, or other elements. In some embodiments, the tubular structures comprise titanium oxide and nickel oxide. The composition of the tubular structures depends in part on the composition of the surface of substrate from which they are formed. The nanostructure can be formed on substantially (e.g. at least about 90%) all of the entire outer surface of a substrate, or it can be formed on a single or multiple discrete locations on the surface of a substrate.

Each of the tubular structures of the first layer has a cylindrical wall with an inner surface, a top surface, and an outer surface, the cylindrical wall defining a lumen therein. The geometry of a tubular structure generally defines an axis that further generally defines a direction of the tubular structure. If a tubular structure were a circular cylinder, then the axis is the locus of the centers of the circles defined by the tubular structure. With tubular structures having a polygonal or irregular cross section, the axis generally follows the center of the tubular structure. Collectively, the top surfaces of the tubular structures define a distal surface of the first layer. In some embodiments, the tubular structures can be aligned generally perpendicular to the substrate and generally parallel to one another (e.g. arranged vertically compared to a horizontal substrate). In other embodiments, at least some of the tubular structures can be formed at an angle other than 90° relative to the substrate. In some embodiments, the tubular structures are immediately adjacent to one another, such that there is no observable space between the outer surface of a cylindrical wall of one tubular structure and the outer surface(s) of the cylindrical wall(s) of the adjacent tubular structure(s). In some embodiments, the outer surface of the cylindrical wall of one tubular structure is in direct contact with the outer surface(s) of the cylindrical wall(s) of the adjacent tubular structure(s). In some embodiments, the outer surface of the cylindrical wall of one tubular structure is integrally connected with the outer surface(s) of the cylindrical wall(s) of the adjacent tubular structure(s). In other embodiments, the tubular structures can be arranged such that there is space between the cylindrical wall of one tubular structure and the cylindrical wall of the adjacent tubular structures. In some embodiments, tubular structures are not cylindrical and can define a variable cross-sectional area along the axial direction. In some embodiments, tubular structures can define polygonal or irregular openings that are approximately or generally perpendicular to the axial direction. The openings can be characterized by major and minor axes and a hydraulic diameter. A hydraulic diameter is a ratio of four times an area divided by a perimeter of a given opening.

The second layer comprises a lattice disposed on top of the distal surface of the first layer. The lattice comprises metal oxide(s). The lattice may or may not further comprise carbon, fluoride, or other elements. This second layer can be in contact with or integrally connected to the distal surface of the first layer (e.g. the top surface of cylindrical walls of the plurality of tubular structures). Compared to the discrete tubular structures of the first layer, the second layer generally comprises a single integrated structure. In some embodiments, the distal surface of the second layer is significantly free of any amorphous material or particulate with dimensions greater than about 30 nm. In some embodiments, the lattice comprises metal oxides including but not limited to titanium oxide and nickel oxide. In some embodiments, the ratio of titanium oxide to nickel oxide on the distal surface (e.g. the top about 10 nm) of the second layer is greater than about 10:1, or about 17:1.

Methods of forming a nanostructure comprising metal oxide on the surface of a substrate are also disclosed herein. In one embodiment, the method comprises placing an anode and at least one cathode in electrical contact through a first electrolyte solution, applying a first voltage across the anode and cathode(s) through the first electrolyte solution for a first time period, modifying or replacing the first electrolyte solution to provide a second electrolyte solution containing an acid, and applying a second voltage across the anode and cathode(s) through the second electrolyte solution for a second time period. In some embodiments, the anode and cathode(s) are optionally provided. In some embodiments, the first electrolyte does not contain an acid or contains a very low amount of acid. The first electrolyte solution may be modified by adding an acid, resulting in the second electrolyte solution. Alternatively, the first electrolyte solution may be removed and replaced with a second electrolyte solution that contains an acid. In some embodiments, the first electrolyte solution may be modified by lowering the pH or increasing the acid concentration to achieve the second electrolyte solution. In some embodiments, the substrate is not modified to remove any portion of the oxide structure(s) formed during the first time period prior to the second time period. The first and second voltages can be the same or different. The first and second time periods can be the same or different. The temperature of the electrolyte solution in the first and second time periods can be the same or different.

In another embodiment, the method comprises placing an anode and at least one cathode in electrical contact through a first electrolyte solution, applying a first voltage across the anode and cathode(s) through the first electrolyte solution for a first time period, removing at least part of the oxide layer formed on the surface of the anode during the first time period, and applying a second voltage across the anode and cathode(s) through the second electrolyte solution for a second time period. In some embodiments, the anode and cathode(s) are optionally provided. The first and second voltages can be the same or different. The first and second time periods can be the same or different. The temperature of the electrolyte solution in the first and second time periods can be the same or different.

In another embodiment, the method comprises placing an anode and at least one cathode in electrical contact through a first electrolyte solution, applying a first voltage across the anode and cathode(s) through the first electrolyte solution for a first time period, removing at least part of the oxide layer formed on the surface of the anode during the first time period, modifying or replacing the first electrolyte solution to provide a second electrolyte solution containing an acid, and applying a second voltage across the anode and cathode(s) through the second electrolyte solution for a second time period. In some embodiments, the anode and cathode(s) are optionally provided. The first electrolyte solution may be modified by adding an acid. Alternatively, the first electrolyte solution may be removed and replaced with a second electrolyte solution that contains an acid. In some embodiments, the first electrolyte solution may be modified by lowering the pH or increasing the acid concentration to achieve the second electrolyte solution. The first and second voltages can be the same or different. The first and second time periods can be the same or different. The temperature of the electrolyte solution in the first and second time periods can be the same or different.

In some embodiments of the methods discussed above, the anode can be an implantable medical device, including but not limited to a stent. The medical device can also be an orthopedic implant, such as a knee implant, bone screw, or bone staple, such as those used for hand and foot bone fragments osteotomy fixation and joint arthrodesis. The cathode can be platinum, iron, stainless steel, graphite, or any other conductive material.

Methods of forming a biocompatible nanostructure on the surface of an implantable medical device are also disclosed herein. In some embodiments, the methods comprise placing an anode and cathode in electrical contact through a first electrolyte solution containing ethylene glycol, water, and ammonium fluoride, applying a first voltage across the anode and cathode through the first electrolyte solution for a first time period, modifying or replacing the first electrolyte solution resulting in a second electrolyte solution containing an acid, and applying a second voltage across the anode and cathode through the second electrolyte solution for a second time period. In some embodiments, an implantable medical device is optionally provided as the anode. In some embodiments, the cathode is optionally provided. In some embodiments, the first electrolyte solution does not contain an acid. In some embodiments, the first electrolyte solution can be modified by adding an acid, including but not limited to sulfuric acid or hydroiodic acid. In other embodiments, the first electrolyte solution can be removed and replaced with a second electrolyte solution that contains an acid, including but not limited to sulfuric acid or hydroiodic acid. The first and second voltages can be the same or different. The first and second time periods can be the same or different. The temperature of the electrolyte solution in the first and second time periods can be the same or different. In some embodiments, the first and second voltages are about 25V, the first and second time periods are about 5 minutes, and the temperature of the electrolyte solution in the first and second time periods is about 30 C. In some embodiments, the oxide material formed during the first time period is not removed or modified prior to the second time period.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

FIG. 11 shows a process flow diagram for one embodiment of a method of forming metal oxide nanostructures on an implantable medical device.

FIG. 18A shows a plot of the total cell count, based on nuclear stain, of primary human aortic endothelial cells on the surface of the nanostructured nitinol coupons compared to the control coupons for each of the time points (24 hours, 48 hours, 72 hours, 96 hours). FIG. 18B shows a plot of the total cell area on the surface of the nanostructured nitinol coupons compared to the control coupons for each of the time points (24 hours, 48 hours, 72 hours, 96 hours). FIG. 18C shows a plot of the nuclei count per substrate for the nanostructured nitinol coupons compared to the control coupons for each of the time points (24 hours, 48 hours, 72 hours, 96 hours). FIG. 18D shows a plot of the total cell area per substrate for the nanostructured nitinol coupons compared to the control coupons for each of the time points (24 hours, 48 hours, 72 hours, 96 hours).

FIG. 19A shows a plot of the total cell count, based on nuclear stain, of human aortic smooth muscle cells on the surface of the nanostructured nitinol coupons compared to the control coupons for each of the time points (24 hours, 48 hours, 72 hours, 96 hours). FIG. 19B shows a plot of the total cell area on the surface of the nanostructured nitinol coupons compared to the control coupons for each of the time points (24 hours, 48 hours, 72 hours, 96 hours). FIG. 19C shows a plot of the nuclei count per substrate for the nanostructured nitinol coupons compared to the control coupons for each of the time points (24 hours, 48 hours, 72 hours, 96 hours). FIG. 19D shows a plot of the total cell area per substrate for the nanostructured nitinol coupons compared to the control coupons for each of the time points (24 hours, 48 hours, 72 hours, 96 hours).

DETAILED DESCRIPTION

Figure 1:
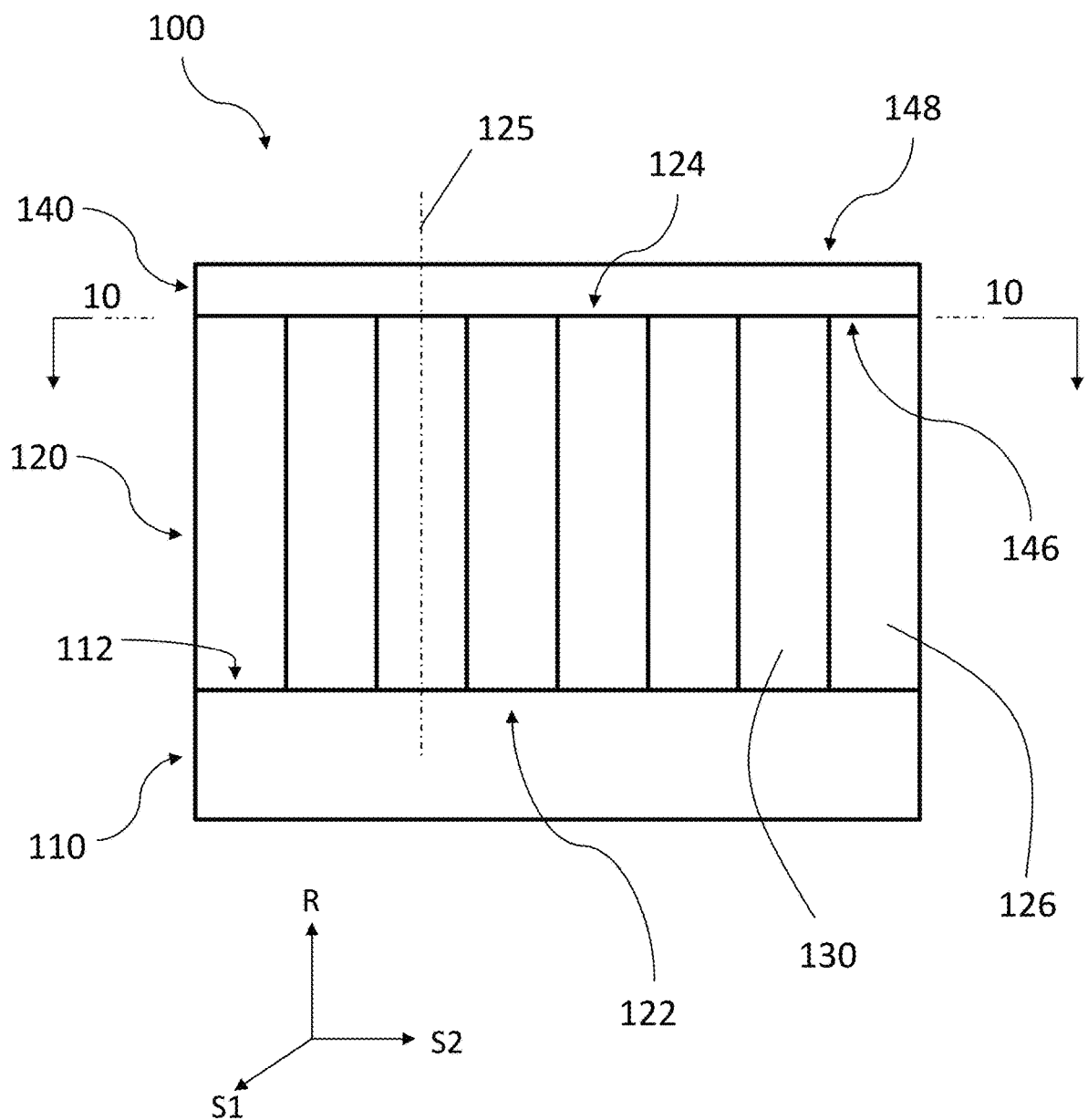
FIG. 1 shows a schematic representation of a side view one embodiment of a metal oxide nanostructure.

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

FIGS. 1-5 illustrate one embodiment of the present metal oxide nanostructure 100. The nanostructure 100 can be formed on substantially (e.g. at least about 90%) all of the entire outer surface of a substrate 110, or it can be formed on a single or multiple discrete locations on the surface of a substrate 110.

The nanostructure 100 includes a nanotube layer 120 situated between a substrate 110 at the nanotube layer's proximal surface 122 and a lattice layer 140 at the nanotube layer's distal surface 124. The nanotube layer includes a plurality of tubular structures 126 arranged generally or approximately parallel to one another, running from the proximal surface of the nanotube layer to the distal surface of the nanotube layer. While the proximal 122 and distal 124 surfaces are shown as planar or smooth, in practice the surfaces 122 and 124 may or may not be somewhat discontinuous. Also, the tubular structures 126 may or may not vary in length and orientation.

Each of the plurality of tubular structures 126 has a cylindrical wall 127 with an inner surface 128, a top surface 129 and an outer surface 130, the inner surface 128 defining lumen 132 therein. Collectively, the top surface 129 of each of the plurality of tubular structures 126 defines the distal surface 124 of the nanotube layer 120. The inner surface 128 defines an inner diameter di, and the outer surface 130 defines an outer diameter do.

Illustrated tubular structures 126 are depicted as right circular cylinders generally aligned with an axis R and perpendicular to surfaces 122 and 124. The right circular cylinders define axes 125 that are defined as the locus of centers of circles defined by the tubular structures. An axis 125 of a right circular cylinder is therefore also perpendicular to surfaces 122 and 124, and the axes 125 are parallel.

The tubular structures 126 are depicted for illustrative purposes as right circular cylinders. However, it is to be understood that tubular structures 126 only approximate right circular cylinders to a variable degree. More generally, the cross sections of tubular structures 126 can be circular, elliptical, polygonal, irregular, or even a variable combination thereof. A defined axis 125 generally follows the cross-sectional center of a tubular structure 126. The axes of the tubular structures are generally or approximately aligned or define acute angles with respect to one another. The axes 125 are generally perpendicular to surfaces 122 and 124 at least to within an acute angle. Also, the cross-sectional geometry of a tubular structure 126 can vary along its axis 125. It is to be understood that in the following illustrative description terms like diameters and axes are approximations to the actual geometry which may embody some degree of variation.

In some embodiments, the tubular structures 126 are immediately adjacent to one another, such that there is no observable space between the outer surface 130 of a cylindrical wall 127 of one tubular structure 126 and the outer surface(s) 130 of the cylindrical wall(s) 127 of the adjacent tubular structure(s) 126. In some embodiments, the outer surface 130 of the cylindrical wall 127 of one tubular structure 126 is in direct contact with the outer surface(s) 130 of the cylindrical wall(s) 127 of the adjacent tubular structure(s) 126. In some embodiments, the outer surface 130 of the cylindrical wall 127 of one tubular structure 126 is integrally connected with the outer surface(s) 126 of the cylindrical wall(s) 127 of the adjacent tubular structure(s) 126. In other embodiments, the tubular structures 126 can be arranged such that there is observable space between the outer surface 130 of the cylindrical wall 127 of one tubular structure 126 and the outer surface 130 of the cylindrical wall 127 of one or more the adjacent tubular structure(s) 126.

In some embodiments, the inner diameter di is approximately constant along the height of a given tubular structure 126. In other embodiments, the inner diameter di changes along the height of a given tubular structure 126, for example the inner diameter di is smaller at the top of the tubular structure 126 than at the bottom of the tubular structure 126. In some embodiments, each of the plurality of tubular structures 126 have generally the same inner diameter. In other embodiments, the tubular structures 126 have varying inner diameters. In some embodiments, each of the plurality of tubular structures have generally the same outer diameter. In other embodiments, the tubular structures 126 have varying outer diameters. In some embodiments, the inner diameters of the tubular structures 126 are in the range of 10-60 nm. In some embodiments, the outer diameters of the tubular structures 126 are in the range of 20-80 nm.

The tubular structures 126 also have a height. In some embodiments, the height is between about 10 nm and 2000 nm. In some embodiments, the height of the tubular structures 126 is about 400 nm, or between about 300 nm to about 500 nm. In other embodiments, the height of the tubular structures may be between about 100 nm and about 500 nm, about 500 nm and about 1000 nm, or about 1000 nm and about 2000 nm. In other embodiments, the height of the tubular structures may be about 50 nm, 100 nm, 150 nm, 200 nm, 250 nm, 300 nm, 350 nm, 450 nm, 500 nm, 550 nm, 600 nm, 650 nm, 700 nm, 750 nm, 800 nm, 850 nm, 900 nm, 950 nm, or 1000 nm.

The tubular structures 126 contain one or more metal oxides. The tubular structures 126 may or may not further contain carbon, fluoride, or other elements. In some embodiments, the metal oxide is titanium oxide. In other embodiments, the metal oxide is nickel oxide. In some embodiments, the metal oxide includes both titanium oxide and nickel oxide. In some embodiments, the ratio of titanium oxide to nickel oxide in the nanotube layer 120 is greater than or about 1:1.

In some embodiments, the ratio of titanium oxide to nickel oxide in the nanotube layer 120 is greater than 1:1. In other embodiments, the ratio of titanium oxide to nickel oxide in the nanotube layer 120 is less than 1:1. In certain embodiments, the ratio of titanium oxide to nickel oxide in the nanotube layer 120 is about 1:1. In some embodiments, the ratio of titanium oxide to nickel oxide in the nanotube layer 120 is greater than about 5:1, or between about 5:1 to about 20:1. In some embodiments, the ratio of titanium oxide to nickel oxide in the nanotube layer 120 is greater than 20:1. In some embodiments, the ratio of titanium oxide to nickel oxide in the nanotube layer 120 is between about 1:1 and 5:1, about 5:1 and 10:1, about 10:1 and 15:1, or about 15:1 and 20:1.

The lattice layer 140 includes a lattice 142 with openings 144 therein. The lattice layer 140 has a proximal surface 146 in contact with or integrally connected to the distal surface 124 of the nanotube layer 120, and a distal surface 148 opposite the proximal surface 146.

In some embodiments, the lattice 142 contains titanium oxide. In other embodiments, the lattice 142 contains nickel oxide. In some embodiments, the lattice 142 contains both titanium oxide and nickel oxide. In some embodiments, the ratio of titanium oxide to nickel oxide on the distal surface 148 of the lattice 142 is greater than 5:1, or about 6:1, 7:1, 8:1, 9:1, 10:1, 11:1, 12:1, 13:1, 14:1 15:1, 16:1, 17:1, 18:1, 19:1 or 20:1. In some embodiments, the ratio of titanium oxide to nickel oxide on the distal surface 148 of the lattice 142 (e.g. the top about 10 nm of the lattice) is about 17:1. In some embodiments, the lattice 142 may or may not further contain carbon, fluoride, or other elements.

In some embodiments, the ratio of titanium oxide to nickel oxide on the distal surface 148 the lattice 142 is greater than 1:1. In other embodiments, the ratio of titanium oxide to nickel oxide on the distal surface 148 of the lattice 142 is less than 1:1. In certain embodiments, the ratio of titanium oxide to nickel oxide on the distal surface 148 of the lattice 142 is about 1:1. In some embodiments, the ratio of titanium oxide to nickel oxide on the distal surface 148 of the lattice 142 is between about 1:1 and 5:1, about 5:1 and 10:1, about 10:1 and 15:1, or about 15:1 and 20:1.

The lattice layer 140 also has a thickness defined as the average distance between the proximal surface 146 and the distal surface 148 of the lattice layer 140. In some embodiments, the thickness is between about 5 nm and 100 nm. In some embodiments, the lattice layer 140 has a thickness of about 50 nm. In other embodiments, the thickness of the lattice layer 140 may be about 5 nm, 10 nm, 15 nm, 20 nm, 25 nm, 30 nm, 35 nm, 40 nm, 45 nm, 55 nm, 60 nm, 65 nm, 70 nm, 75 nm, 80 nm, 85 nm, 90 nm, 95 nm, or 100 nm.

Figure 6:
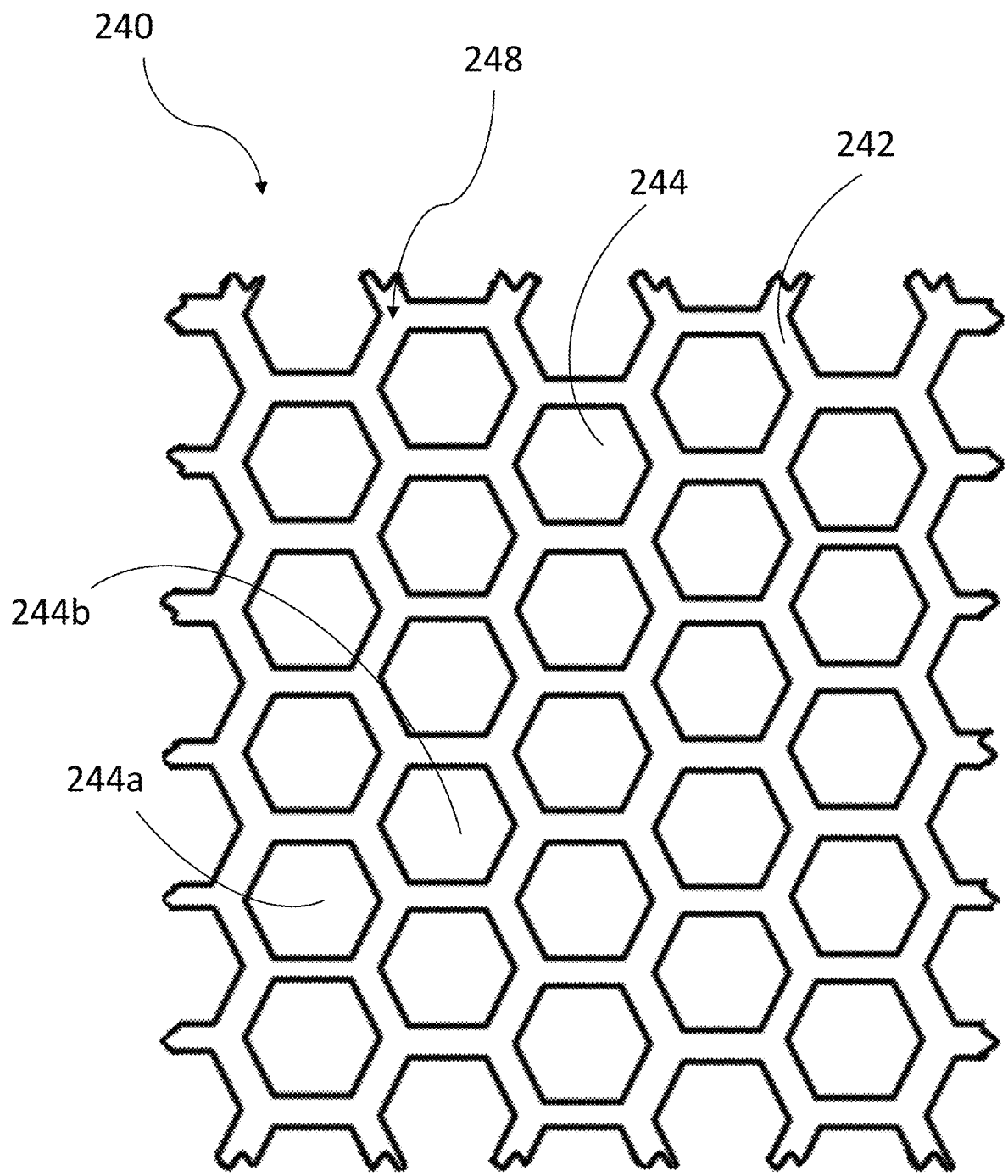
FIG. 6 shows a schematic representation of a top view of one embodiment of the lattice layer in FIG. 1.
Figure 7:
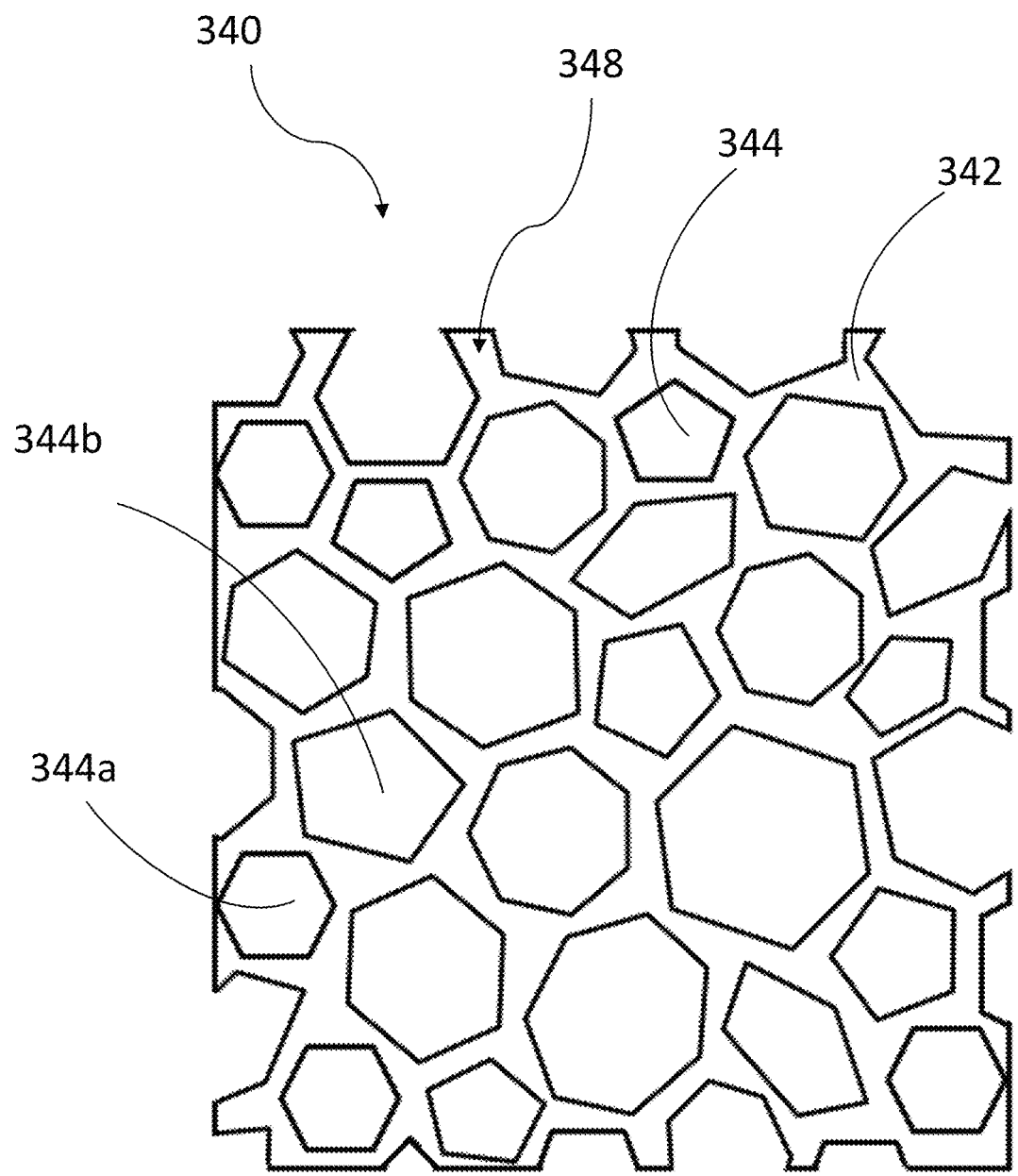
FIG. 7 shows a schematic representation of a top view of another embodiment of the lattice layer in FIG. 1.

The openings 144 are generally polygonal or irregular (as shown in FIGS. 6 and 7 as elements 244 and 344) in shape viewed from above the distal surface 148 of the lattice layer 140, although in certain embodiments at least some of the openings 144 may appear to be elliptical or circular when viewed from above the distal surface 148 of the lattice layer 140. The openings 144 can be irregularly or variably sized, shaped, and spaced as viewed from the distal surface 148 of the lattice layer 140. However, in certain embodiments, the openings 144 can be nearly identical in size, shape, and spacing. In certain embodiments, the average space as measured from the center of one openings 144a to the center of an adjacent openings 144b is approximately 40 nm.

The openings 144 have a hydraulic diameter or a lateral dimension when they are not circular. A hydraulic diameter is defined as a ratio of four times an area divided by a perimeter for a given opening. In discussing diameters before and hereafter these can be actual diameter, hydraulic diameters, or some interpolation between a major and minor axis of the opening. In some embodiments, the openings 144 have varying diameters. In other embodiments, the openings 144 have generally the same size diameters. In some embodiments, a majority of the diameters of the openings 144 are in the range of about 10 nm to about 60 nm, or about 20 nm to about 40 nm. In some embodiments a majority of the diameters of the openings 144 can be less than about 10 nm or greater than about 60 nm. In some embodiments, the average diameter of the openings 144 is about 30 nm.

In some embodiments, the centers of the openings 144 are not aligned with the axes 125 of the tubular structures 126 below. Rather, the nanotube layer 120 and lattice layer 140 can be offset such that the centers of some of the openings 144 will align with the axes 125 below (e.g. the openings 144 and lumens 132 are generally concentric when view from above the distal surface 148), while the centers of other openings 144 will not align with the axes 125 below (e.g. the openings 144 and lumens 132 are generally nonconcentric). In some embodiments, depending on the size, shape, and spacing of the openings 144, a majority of the openings 144 can be generally aligned (e.g. the openings 144 and lumens 132 are generally concentric when viewed from above the distal surface 148) with the lumens 132 of the tubular structures 126 of the nanotube layer 120 below the lattice layer 140. In other embodiments, a majority of the openings 144 can be generally unaligned with the lumens 132 (e.g. the openings 144 and lumens 132 are generally nonconcentric). Stated another way, the axes of the tubular structures 126 may not be centered upon the openings 144.

The metal oxide nanostructure 100 can be formed on the surface 112 of a substrate 110 via an electrochemical anodization process. In some embodiments, the substrate 110 can be the outer surface of an implantable medical device, such as a stent. The substrate 110 can also be an orthopedic implant, such as a knee implant, bone screw, or bone staple, such as those used for hand and foot bone fragments osteotomy fixation and joint arthrodesis. In some embodiments, substrate 110 can be a metal such as titanium, or a titanium alloy including but not limited to a nickel titanium alloy. In certain embodiments, the substrate 110 is made of a nickel titanium alloy in which the ratio of nickel to titanium near the surface is approximately 1:1. In certain embodiments, the substrate 110 can be a layer of titanium or a titanium alloy, including but not limited to a nickel titanium alloy, on the outer surface of an implantable medical device. In some embodiments, the outer surface of a substrate 110 may be an oxide layer (e.g. titanium oxide). The nanostructure 100 can be formed on the entire outer surface of the substrate 110, or the nanostructure 100 can be formed on only certain portions of the surface of the substrate 110.

Figure 2:
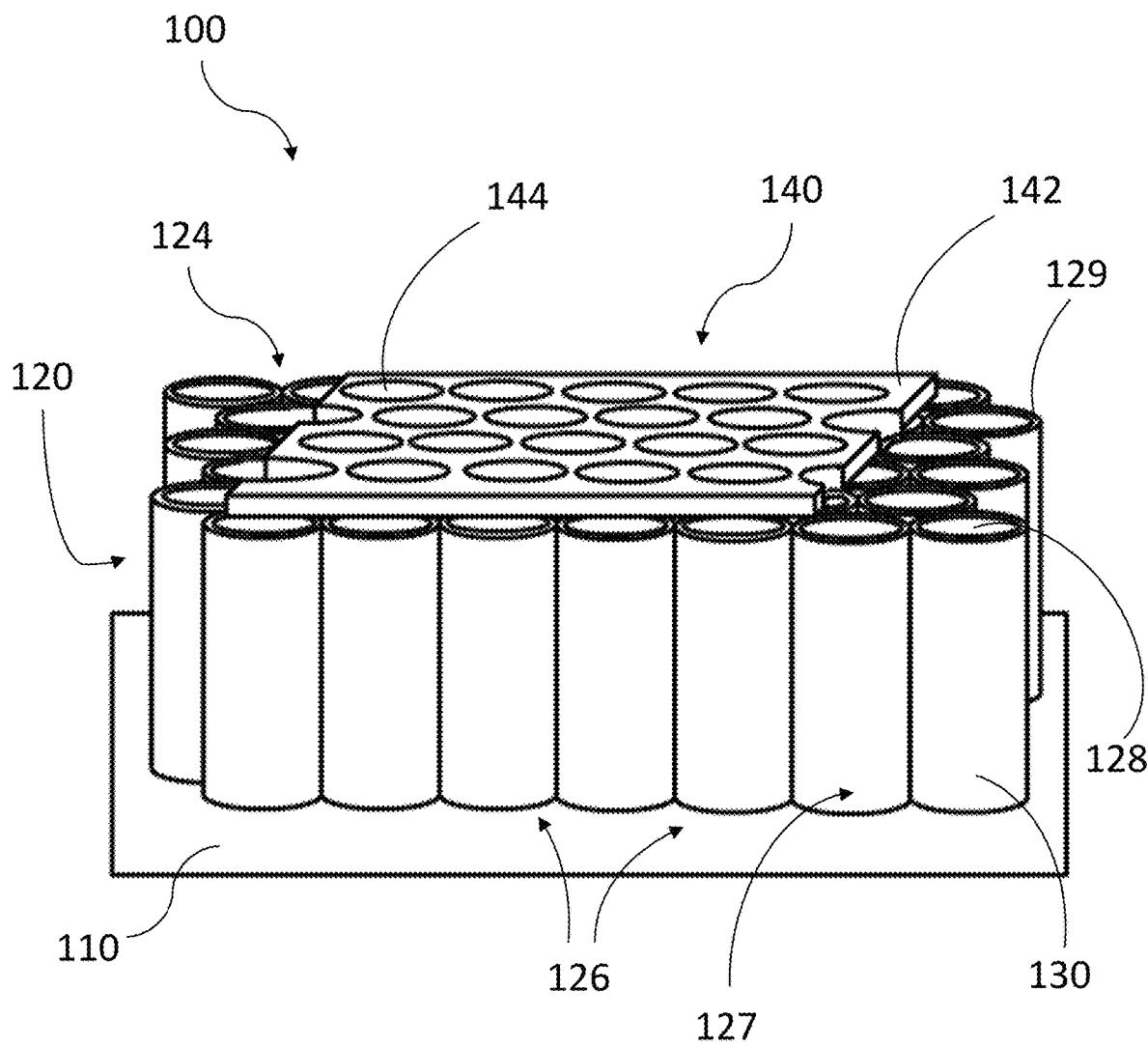
FIG. 2 shows a schematic representation of a partial side and top profile view of the metal oxide nanostructure of FIG. 1.
Figure 3:
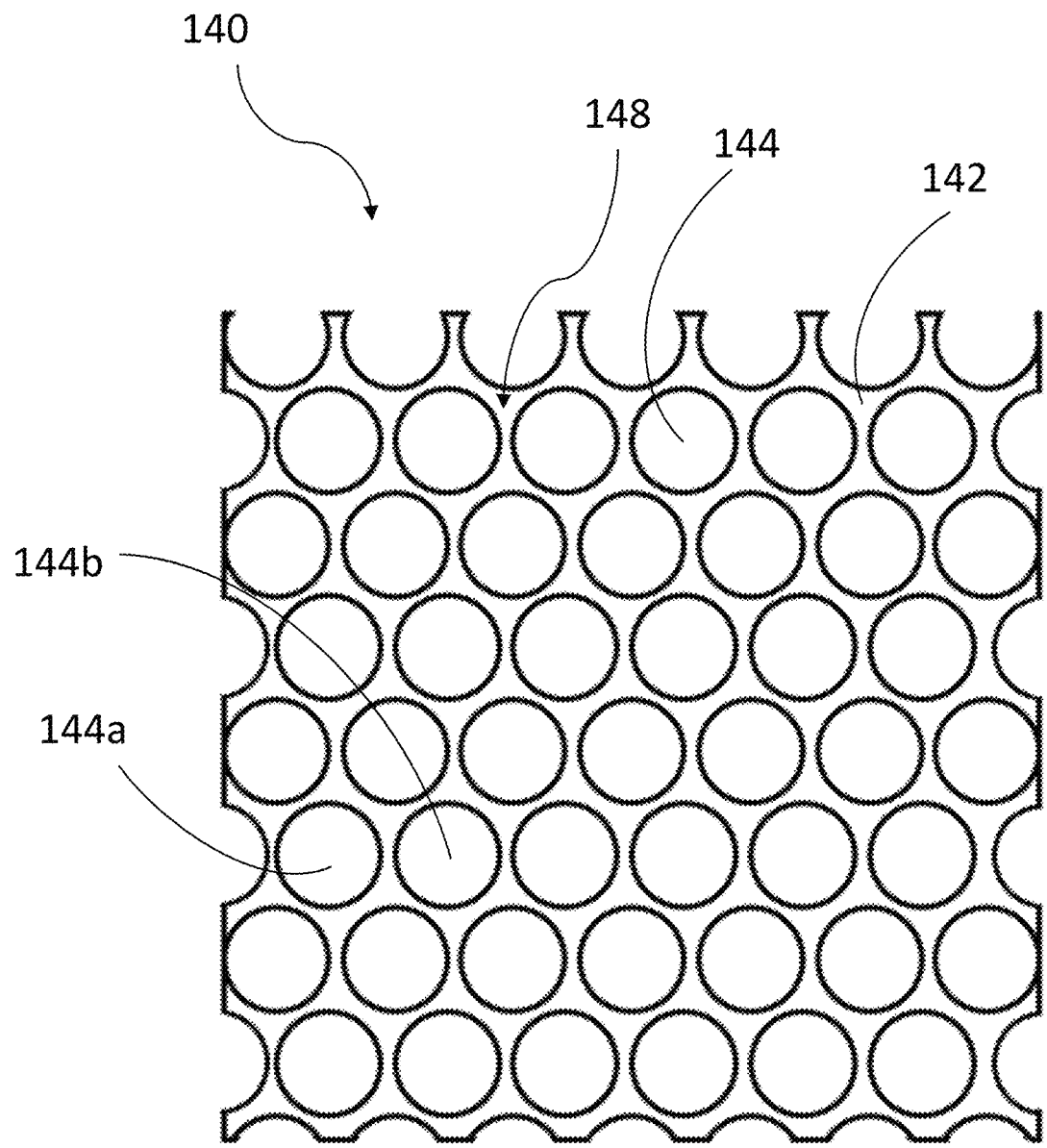
FIG. 3 shows a schematic representation of a top view of the lattice layer of the metal oxide nanostructure of FIG. 1.
Figure 4:
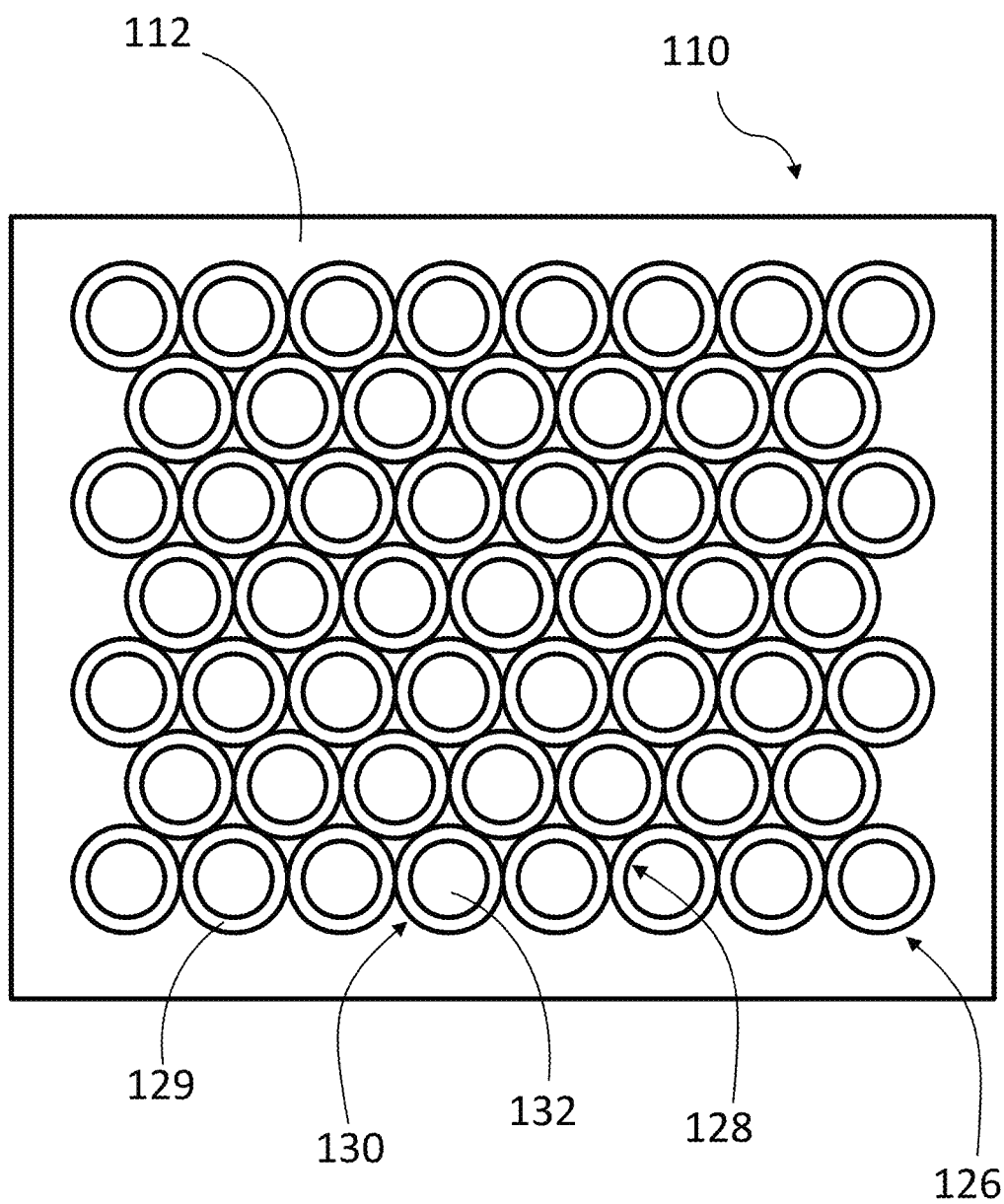
FIG. 4 shows a cross-sectional view of the metal oxide nanostructure of FIG. 1 as viewed along plane 10-10.
Figure 5:
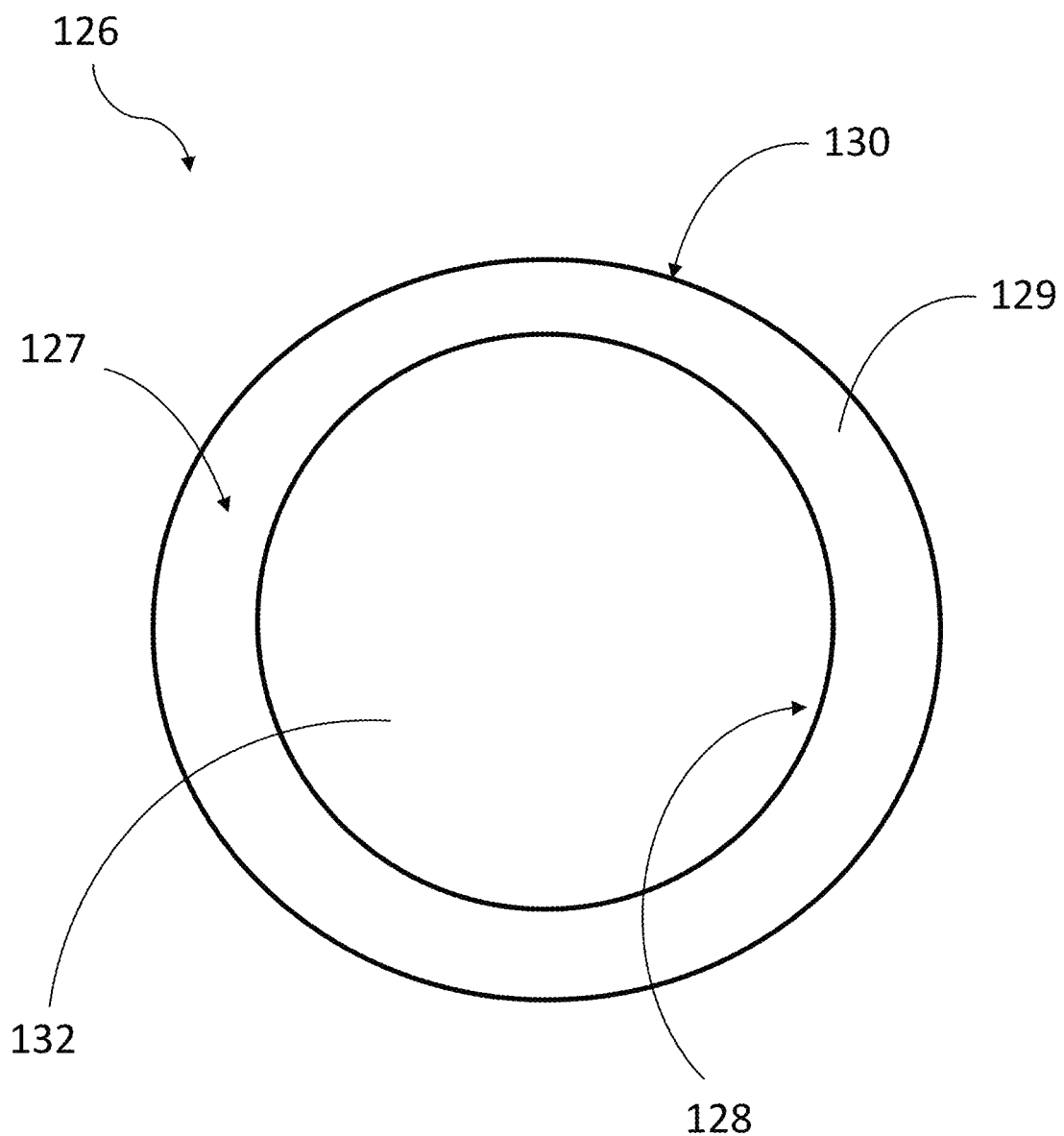
FIG. 5 shows a schematic representation of a top view of a single tubular structure from the nanotube layer of the metal oxide nanostructure of FIG. 1.

FIG. 6 illustrates an alternate embodiment of the lattice layer shown in FIGS. 1-3 with respect to the general shape and arrangement of the openings 244. The lattice layer 240 contains metal oxides. The lattice layer 240 may or may not further contain carbon, fluoride, or other elements. The metal oxide material of the lattice layer 240 defines the openings 244 and forms a lattice 242. In some embodiments, the lattice 242 contains titanium oxide. In other embodiments, the lattice 242 contains nickel oxide. In some embodiments, the lattice 242 contains both titanium oxide and nickel oxide. In some embodiments, the ratio of titanium oxide to nickel oxide on the distal surface 248 of the lattice 242 is greater than 5:1, or about 6:1, 7:1, 8:1, 9:1, 10:1, 11:1, 12:1, 13:1, 14:1 15:1, 16:1, 17:1, 18:1, 19:1 or 20:1. In some embodiments, the ratio of titanium to nickel oxide on the distal surface 248 of the lattice 242 (e.g. the top about 10 nm of the lattice) is about 17:1.

The openings 244 are generally polygonal in shape viewed from above the distal surface 248 of the lattice layer 240. The openings 244 can be irregularly sized, shaped, and spaced as viewed from the distal surface 248 of the lattice layer 240. However, in certain embodiments, the openings 244 can be nearly identical in size, shape, and spacing. In certain embodiments, the average space as measured from the center of one openings 244a to the center of an adjacent openings 244b is approximately 40 nm.

FIG. 7 illustrates an alternate embodiment of the lattice layer shown in FIGS. 1-3 with respect to the general shape and arrangement of the openings 344. The lattice layer 340 contains metal oxides. The lattice layer 340 may or may not further contain carbon, fluoride, or other elements. The metal oxide material of the lattice layer 340 defines the openings 344 and forms a lattice 342. In some embodiments, the lattice 342 contains titanium oxide. In other embodiments, the lattice 342 contains nickel oxide. In some embodiments, the lattice 342 contains both titanium oxide and nickel oxide. In some embodiments, the ratio of titanium oxide to nickel oxide on the distal surface 348 of the lattice 342 is greater than 5:1, or about 6:1, 7:1, 8:1, 9:1, 10:1, 11:1, 12:1, 13:1, 14:1 15:1, 16:1, 17:1, 18:1, 19:1 or 20:1. In some embodiments, the ratio of titanium to nickel oxide on the distal surface 348 of the lattice 342 (e.g. the top about 10 nm of the lattice) is about 17:1.

The openings 344 are generally polygonal in shape viewed from above the distal surface 348 of the lattice layer 340. As shown in FIG. 7, the openings 344 can be irregularly sized, shaped, and spaced as viewed from the distal surface 348 of the lattice layer 340. In certain embodiments, the average space as measured from the center of one openings 344a to the center of an adjacent openings 344b is approximately 40 nm.

Figure 8:
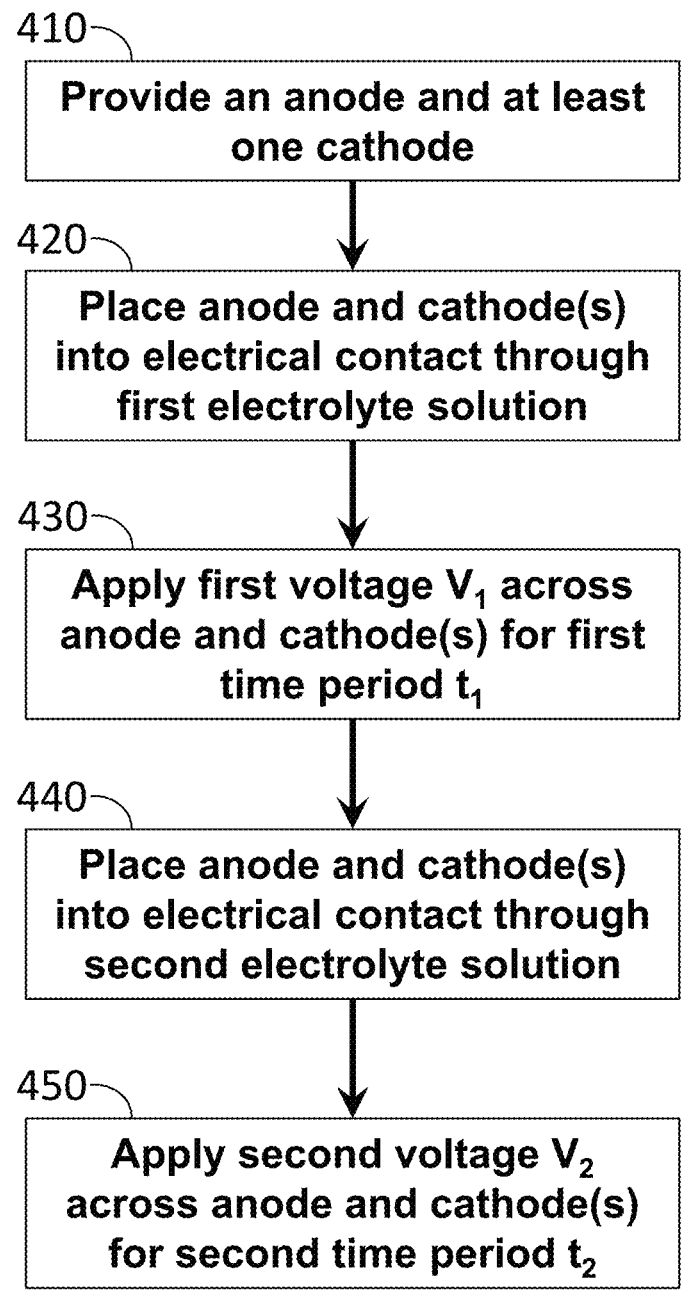
FIG. 8 shows a process flow diagram for one embodiment of a method of forming metal oxide nanostructures.

FIG. 8 shows a process flow diagram for one embodiment of a method of forming metal oxide nanostructures. At block 410, an anode and at least one cathode are optionally provided. In some embodiments, the anode contains an alloy of nickel and titanium. In some embodiments, the anode contains an alloy of nickel and titanium, with a ratio of nickel to titanium of approximately 1:1. In some embodiments, the anode can be an implantable medical device, including but not limited to a stent. The anode can also be an orthopedic implant, such as a knee implant, bone screw, or bone staple, such as those used for hand and foot bone fragments osteotomy fixation and joint arthrodesis. The at least one cathode(s) can be made from any suitable material, including but not limited to platinum, iron, stainless steel, or graphite. If more than one cathode is used, they can be positioned such that they are a similar distance from the anode, and optionally in a symmetrical fashion, and the setup can optionally include a reference electrode.

At block 420, the anode and cathode(s) are placed in electrical contact through a first electrolyte solution. The first electrolyte includes an organic solvent, a fluoride-bearing species, and an oxygen source. The oxygen source can be water, or it can be any other single oxygen donor compound, such as methanol. In some embodiments, the first electrolyte may or may not also optionally contain other additives, such as buffers, surfactants, biocides, salts, and corrosion inhibitors. The first electrolyte may or may not also optionally contain an acid, so long as the acid is weak enough or present at a low enough concentration such that it does not interfere with the formation of the nanostructure. In some embodiments, the first electrolyte does not contain an acid.

The organic solvent can be ethylene glycol. Suitable solvents for use herein include organic solvents, but are not limited to, aliphatic alcohols, aromatic alcohols, diols, glycol ethers, poly(glycol)ethers, lactams, formamides, acetamides, long chain alcohols, ethylene glycol, propylene glycol, diethylene glycols, triethylene glycols, glycerol, dipropylene glycols, glycol butyl ethers, polyethylene glycols, polypropylene glycols, amides, ethers, carboxylic acids, esters, organosulfides, organosulfoxides, sulfones, alcohol derivatives, carbitol, butyl carbitol, cellosolve, ether derivatives, amino alcohols, and ketones. Specific examples of organic solvents include, but are not limited to, a polyhydric alcohol, such as ethylene glycol, diethylene glycol, triethylene glycol, tetraethylene glycol, and polyethylene glycols; a polyhydric alcohol ether, such as ethylene glycol monomethylether, ethylene glycol monoethylether, ethylene glycol monobutylether, diethylene glycol monoethylether, diethylene glycol monobutyl ether, and ethylene glycol monophenyl ether; a nitrogen-containing solvent, such as N-methyl-2-pyrrolidone, a substituted pyrrolidone, and mono-, di-, and tri-ethanolamine; or mixtures thereof. The electrolyte may also include nitrogen-containing ketones, such as 2-pyrrolidone, hydroxyethyl-2-pyrrolidone, 1,3-dimethylimidazolid-2-one, and octyl-pyrrolidone; diols, such as ethanediols, propanediols including 1,2-propanediol, 1,3-propanediol, 2-ethyl-2-hydroxymethyl-1,3-propanediol, and ethylhydroxypropanediol, butanediols including 1,2-butanediol, 1,3-butanediol, and 1,4-butanediol, pentanediols including 1,2-pentanediol, and 1,5-pentanediol, hexanediols including 1,2-hexanediol, 1,6-hexanediol, and 2,5-hexanediol, heptanediols including 1,2-heptanediol, and 1,7-heptanediol, octanediols including 1,2-octanediol and 1,8-octanediol; alcohols, such as C1-C6 alcohols including methanol, ethanol, propanol, butanol, pentanol, and hexanol, including isomers thereof such as 1-propanol and 2-propanol; glycol ethers and thioglycol ethers such as polyalkylene glycols including, but not limited to, propylene glycols such as dipropylene glycol, tripropylene glycol, and tetrapropylene glycol; polymeric glycols such as PEG 200, PEG 300, and PEG 400; thiodiglycol; and mixtures thereof. Additional solvents that may be used include hydantoins and derivatives thereof, dimethyl sulfoxide, dimethyl sulfone, tetramethylene sulfone, butanetriols such as 1,2,4-butanetriol, acetic acid, and polyalkoxylated triols. Ionic liquids, such as 1-n-butyl-3-methyl-imidazolium tetrafluoroborate may also be used, but they are not preferred due to their high cost.

Suitable fluoride-bearing species include ammonium fluoride, ammonium bifluoride, potassium fluoride, sodium fluoride, calcium fluoride, magnesium fluoride, and alkylated ammonium fluorides such as tetrabutylammonium fluoride, among others.

Suitable solvents and fluoride-bearing species for use herein are the same as those described for the first anodization step. Suitable acids for use herein include mineral acids and organic acids. Examples of mineral acids include, but are not limited to, HF, HCl, HBr, HI, $H_3PO_4$, $HNO_3$, and $H_2SO_4$. Examples of organic acids include carboxylic acids, including formic acid, adipic acid, fumaric acid, tartaric acid, citric acid, oxalic acid, lactic acid, acetic acid, trifluoroacetic acid, and others.

The first electrolyte solution can be maintained at a relatively constant temperature. The temperature of the first electrolyte solution can be between about 10° and 50° Celsius. In some embodiments, the temperature can be between about 20° and 40° Celsius.

In some embodiments, the first electrolyte solution includes about 99.2 vol % organic solvent and about 0.8 vol % water, about 0.18 wt % fluoride-bearing species, and is maintained at about 30° C. In certain embodiments, the first electrolyte solution includes 99.2 ml organic solvent, 0.2 g fluoride salt, and 0.8 ml water, and is maintained at about 30° C.

At block 430, a first voltage $V_1$ is applied across the anode and cathode through the first electrolyte solution for a first time period $t_1$. The first voltage $V_1$ can be between about 10V and about 60V. In some embodiments, the first voltage $V_1$ is about 25V. In some embodiments, the first voltage applied across the anode and cathode is constant for the first time period $t_1$. In other embodiments, the first voltage applied across the anode and cathode varies over time throughout the first time period $t_1$, as for example when the anodization is run in a galvanostatic mode. The first time period $t_1$ can be between about 1 minute and about 120 minutes. In some embodiments, the first time period $t_1$ is approximately 5 minutes. In some embodiments, the first time period $t_1$ is less than 5 minutes. In other embodiments, the first time period is greater than 5 minutes, including about 6, 7, 8, 9, or 10 minutes. In some embodiments, the first time period is greater than 10 minutes and less than 60 minutes. In some embodiments, the first time period is greater than 60 minutes.

At block 440, the anode and cathode(s) are placed in electrical contact through a second electrolyte solution. The second electrolyte solution includes an organic solvent, a fluoride-bearing species, an oxygen source, and an acid. The organic solvent can be ethylene glycol. In some embodiments, the fluoride salt can be ammonium fluoride. The oxygen source can be water, or it can be any other single oxygen donor compound, such as methanol. The acid can be selected from the group consisting of $H_2SO_4$, HF, HCl, HBr, HI, $H_3PO_4$, $HNO_3$, formic acid, adipic acid, fumaric acid, tartaric acid, citric acid, oxalic acid, lactic acid, acetic acid, trifluoroacetic acid, and others. In some embodiments, the acid is sulfuric acid ($H_2SO_4$). In some embodiments, the acid is hydroiodic acid (HI). The second electrolyte solution includes greater than about 90 vol % organic solvent, about 0.8 vol % water, about 0.001-9.0 vol % acid, and about 0.18 wt % fluoride-bearing species. The appropriate percentage of acid in the second electrolyte solution depends on many factors including the acid(s) used and the molecular weight and pKa of said acid(s). The second electrolyte solution can be maintained at a relatively constant temperature. The temperature of the second electrolyte solution can be between about 10° and 50° Celsius. In some embodiments, the temperature of the second electrolyte solution is about 30° C. In some embodiments, the first electrolyte solution may be modified by lowering the pH or increasing the acid concentration to achieve the second electrolyte solution.

At block 450, a second voltage $V_2$ is applied across the anode and cathode through the second electrolyte solution for a second time period. In some embodiments, the second voltage is about 25V. In some embodiments, the second voltage $V_2$ is constant throughout the second time period $t_2$. In other embodiments, the second voltage $V_2$ varies throughout the second time period $t_2$. The second time period $t_2$ can be between about 1 minute and about 120 minutes. In some embodiments, the second time period $t_2$ is approximately 5 minutes. In some embodiments, the second time period $t_2$ is less than 5 minutes. In other embodiments, the second time period $t_2$ is greater than 5 minutes, including about 6, 7, 8, 9, or 10 minutes. In some embodiments, the second time period $t_2$ is greater than 10 minutes and less than 60 minutes. In some embodiments, the second time period $t_2$ is greater than 60 minutes.

Under suboptimal conditions (e.g. suboptimal acidity in second electrolyte solution, suboptimal voltage $V_1$ or $V_2$, suboptimal temperature, or suboptimal first or second time period $t_1$ or $t_2$), pitting corrosion and/or amorphous material or particulate may or may not be observed. In some embodiments, pitting corrosion and/or amorphous material or particulate are substantially absent from the resulting surface.

Figure 9:
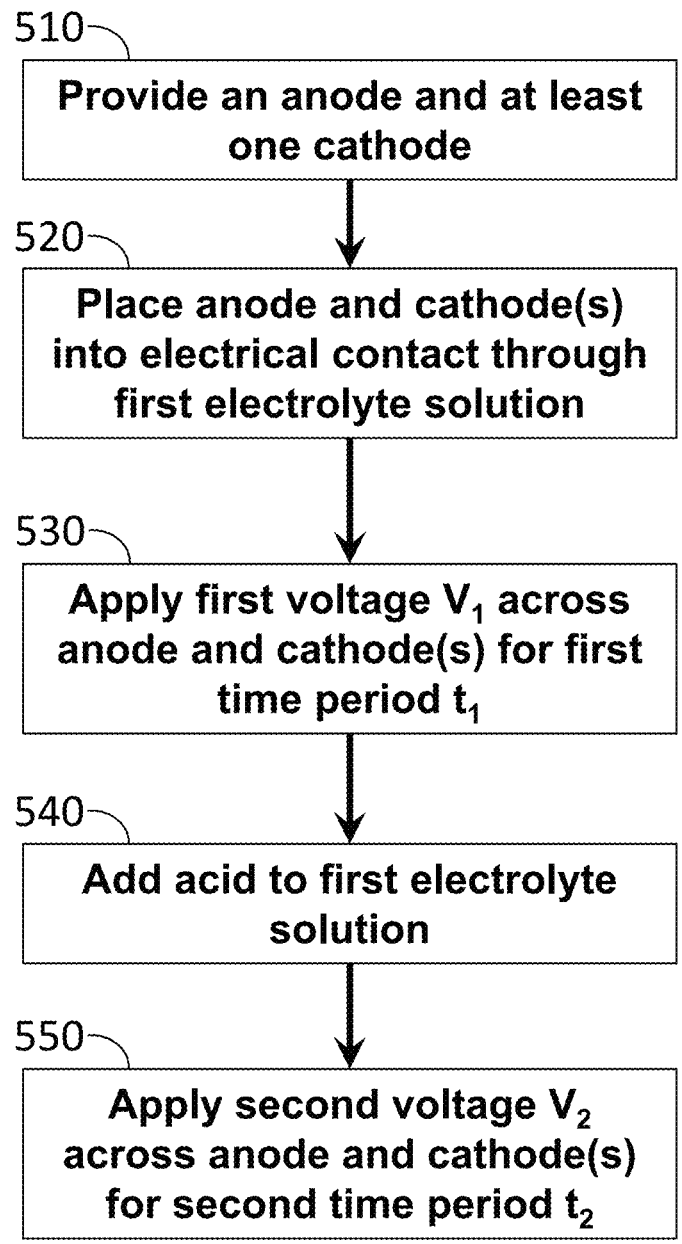
FIG. 9 shows a process flow diagram for another embodiment of a method of forming metal oxide nanostructures.

FIG. 9 shows a process flow diagram for another embodiment of a method of forming metal oxide nanostructures. At block 510, an anode and at least one cathode are optionally provided. In some embodiments, the anode contains an alloy of nickel and titanium. In some embodiments, the anode contains an alloy of nickel and titanium, with a ratio of nickel to titanium of approximately 1:1. In some embodiments, the anode can be an implantable medical device, including but not limited to a stent. The anode can also be an orthopedic implant, such as a knee implant, bone screw, or bone staple, such as those used for hand and foot bone fragments osteotomy fixation and joint arthrodesis. The at least one cathode(s) can be made from any suitable material, including but not limited to platinum, iron, stainless steel, or graphite. If more than one cathode is used, they can be positioned such that they are a similar distance from the anode, and optionally in a symmetrical fashion, and the setup can optionally include a reference electrode.

At block 520, the anode and cathode(s) are placed in electrical contact through a first electrolyte solution. The first electrolyte solution includes an organic solvent, a fluoride-bearing species, and an oxygen source. The organic solvent can be ethylene glycol. In some embodiments, the fluoride-bearing species can be ammonium fluoride. The oxygen source can be water, or it can be any other single oxygen donor compound, such as methanol. In some embodiments, the first electrolyte does not include an acid. In some embodiments, the first electrolyte solution includes about 99.2 vol % organic solvent and about 0.8 vol % water, and about 0.18 wt % fluoride-bearing species. The first electrolyte solution can be maintained at a relatively constant temperature. The temperature of the first electrolyte solution can be between about 10° and 50° Celsius. In some embodiments, the temperature of the first electrolyte solution is about 30° C.

At block 530, a first voltage $V_1$ is applied across the anode and cathode through the first electrolyte solution for a first time period $t_1$. The first voltage $V_1$ can be between about 10V and about 60V. In some embodiments, the first voltage $V_1$ is about 25V. In some embodiments, the first voltage applied across the anode and cathode is constant for the first time period $t_1$. In other embodiments, the first voltage applied across the anode and cathode varies over time throughout the first time period $t_1$, as for example when the anodization is run in a galvanostatic mode.

The first time period $t_1$ can be between about 1 minute and about 120 minutes. In some embodiments, the first time period $t_1$ is approximately 5 minutes. In some embodiments, the first time period $t_1$ is less than 5 minutes. In other embodiments, the first time period is greater than 5 minutes, including about 6, 7, 8, 9, or 10 minutes. In some embodiments, the first time period is greater than 10 minutes and less than 60 minutes. In some embodiments, the first time period is greater than 60 minutes.

At block 540, the first electrolyte solution is modified by adding an acid resulting in a second electrolyte solution. The acid can be selected from the group consisting of $H_2SO_4$, HF, HCl, HBr, HI, $H_3PO_4$, $HNO_3$, formic acid, adipic acid, fumaric acid, tartaric acid, citric acid, oxalic acid, lactic acid, acetic acid, trifluoroacetic acid, and others. In some embodiments, the acid is sulfuric acid ($H_2SO_4$). In some embodiments, the acid is hydroiodic acid (HI). The second electrolyte solution includes greater than about 90 vol % organic solvent, about 0.8 vol % water, about 0.001-9.0 vol % acid, and fluoride-bearing species (wt % dependent on acid used in second electrolyte solution). The appropriate percentage of acid in the second electrolyte solution depends on many factors including the acid(s) used and the molecular weight and pKa of said acid(s). The second electrolyte solution can be maintained at a relatively constant temperature. The temperature of the second electrolyte solution can be between about 10° and 50° Celsius. In some embodiments, the temperature of the second electrolyte solution is about 30° C. In an alternate embodiment, the first electrolyte solution may be modified by lowering the pH or increasing the acid concentration.

At block 550, a second voltage $V_2$ is applied across the anode and cathode through the second electrolyte solution for a second time period $t_2$. The second voltage $V_2$ can be between about 10V and about 60V. In some embodiments, the second voltage $V_2$ is about 25V. In some embodiments, the second voltage $V_2$ is constant throughout the second time period $t_2$. In other embodiments, the second voltage $V_2$ varies throughout the second time period $t_2$. The second time period $t_2$ can be between about 1 minute and about 120 minutes. In some embodiments, the second time period $t_2$ is approximately 5 minutes. In some embodiments, the second time period $t_2$ is less than 5 minutes. In other embodiments, the second time period $t_2$ is greater than 5 minutes, including about 6, 7, 8, 9, or 10 minutes. In some embodiments, the second time period $t_2$ is greater than 10 minutes and less than 60 minutes. In some embodiments, the second time period $t_2$ is greater than 60 minutes.

Under suboptimal conditions (e.g. suboptimal acidity in second electrolyte solution, suboptimal voltage $V_1$ or $V_2$, suboptimal temperature, or suboptimal first or second time period $t_1$ or $t_2$), pitting corrosion and/or amorphous material or particulate may or may not be observed. In some embodiments, pitting corrosion and/or amorphous material or particulate are substantially absent from the resulting surface.

Figure 10:
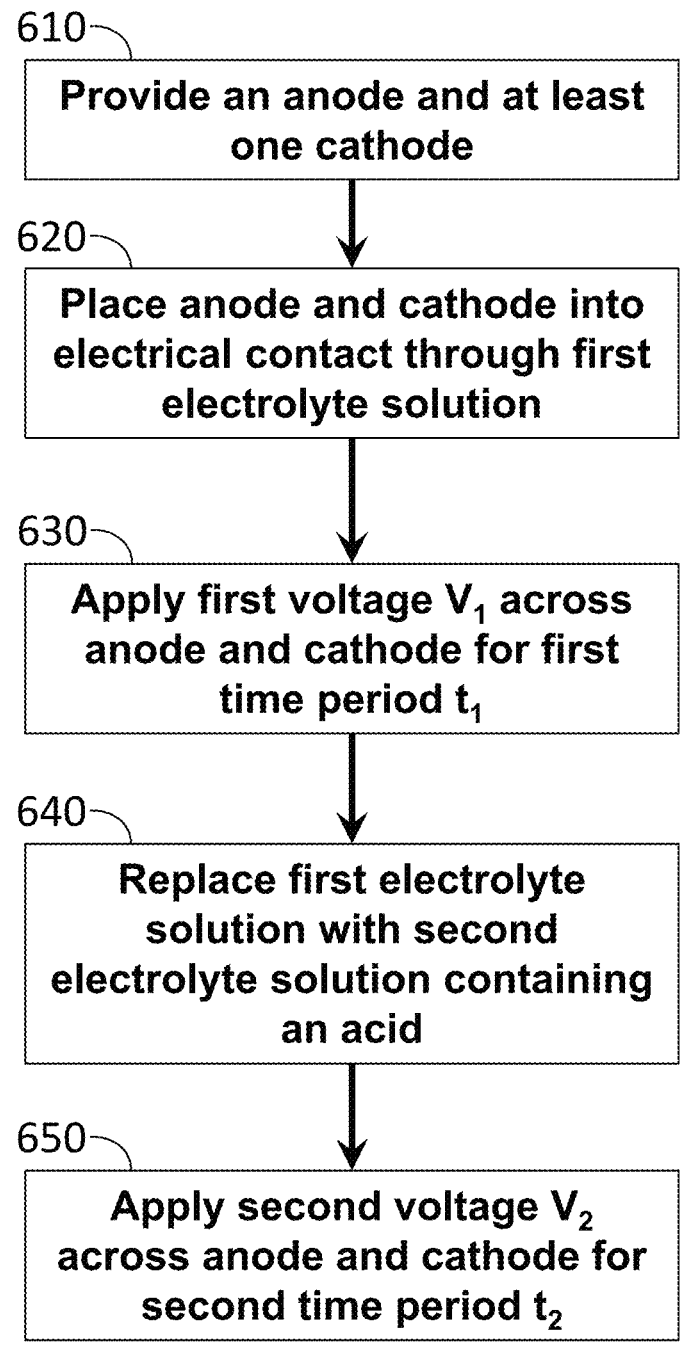
FIG. 10 shows a process flow diagram for another embodiment of a method of forming metal oxide nanostructures.

FIG. 10 shows a process flow diagram for another embodiment of a method of forming metal oxide nanostructures. At block 610, an anode and at least one cathode are optionally provided. In some embodiments, the anode contains an alloy of nickel and titanium. In some embodiments, the anode contains an alloy of nickel and titanium, with a ratio of nickel to titanium of approximately 1:1. In some embodiments, the anode can be an implantable medical device, including but not limited to a stent. The anode can also be an orthopedic implant, such as a knee implant, bone screw, or bone staple, such as those used for hand and foot bone fragments osteotomy fixation and joint arthrodesis. The at least one cathode(s) can be made from any suitable material, including but not limited to platinum, iron, stainless steel, or graphite. If more than one cathode is used, they can be positioned such that they are a similar distance from the anode, and optionally in a symmetrical fashion, and the setup can optionally include a reference electrode.

At block 620, the anode and cathode(s) are placed in electrical contact through a first electrolyte solution. The first electrolyte solution includes an organic solvent, a fluoride-bearing species, and an oxygen source. The organic solvent can be ethylene glycol. In some embodiments, the fluoride-bearing species can be ammonium fluoride. The oxygen source can be water, or it can be any other single oxygen donor compound, such as methanol. In some embodiments, the first electrolyte does not include an acid. In some embodiments, the first electrolyte solution includes about 99.2 vol % organic solvent and 0.8 vol % water, and about 0.18 wt % fluoride-bearing species. The first electrolyte solution can be maintained at a relatively constant temperature. The temperature of the first electrolyte solution can be between about 10° and 50° Celsius. In some embodiments, the temperature of the first electrolyte solution is about 30° C.

At block 630, a first voltage $V_1$ is applied across the anode and cathode through the first electrolyte solution for a first time period $t_1$. The first voltage $V_1$ can be between about 10V and about 60V. In some embodiments, the first voltage $V_1$ is about 25V. In some embodiments, the first voltage applied across the anode and cathode is constant for the first time period $t_1$. In other embodiments, the first voltage applied across the anode and cathode varies over time throughout the first time period $t_1$, as for example when the anodization is run in a galvanostatic mode.

The first time period $t_1$ can be between about 1 minute and about 120 minutes. In some embodiments, the first time period $t_1$ is approximately 5 minutes. In some embodiments, the first time period $t_1$ is less than 5 minutes. In other embodiments, the first time period is greater than 5 minutes, including about 6, 7, 8, 9, or 10 minutes. In some embodiments, the first time period is greater than 10 minutes and less than 60 minutes. In some embodiments, the first time period is greater than 60 minutes.

At block 640, the first electrolyte solution is removed and replaced a second electrolyte solution including an organic solvent, a fluoride-bearing species, an oxygen source, and an acid. The organic solvent can be ethylene glycol. In some embodiments, the fluoride-bearing species can be ammonium fluoride. The oxygen source can be water, or it can be any other single oxygen donor compound, such as methanol. The acid can be selected from the group consisting of $H_2SO_4$, HF, HCl, HBr, HI, $H_3PO_4$, $HNO_3$, formic acid, adipic acid, fumaric acid, tartaric acid, citric acid, oxalic acid, lactic acid, acetic acid, trifluoroacetic acid, and others. In some embodiments, the acid is sulfuric acid ($H_2SO_4$). In some embodiments, the acid is hydroiodic acid (HI). The second electrolyte solution includes greater than about 90 vol % organic solvent, about 0.8 vol % water, about 0.001-9.0 vol % acid, and fluoride-bearing species (wt % dependent on acid used in second electrolyte solution). The appropriate percentage of acid in the second electrolyte solution depends on many factors including the acid(s) used and the molecular weight and pKa of said acid(s). The second electrolyte solution can be maintained at a relatively constant temperature. The temperature of the second electrolyte solution can be between about 10° and 50° Celsius. In some embodiments, the temperature of the second electrolyte solution is about 30° C.

At block 650, a second voltage $V_2$ is applied across the anode and cathode through the second electrolyte solution for a second time period $t_2$. The second voltage $V_2$ can be between about 10V and about 60V. In some embodiments, the second voltage $V_2$ is about 25V. In some embodiments, the second voltage $V_2$ is constant throughout the second time period $t_2$. In other embodiments, the second voltage $V_2$ varies throughout the second time period $t_2$. The second time period $t_2$ can be between about 1 minute and about 120 minutes. In some embodiments, the second time period $t_2$ is approximately 5 minutes. In some embodiments, the second time period $t_2$ is less than 5 minutes. In other embodiments, the second time period $t_2$ is greater than 5 minutes, including about 6, 7, 8, 9, or 10 minutes. In some embodiments, the second time period $t_2$ is greater than 10 minutes and less than 60 minutes. In some embodiments, the second time period $t_2$ is greater than 60 minutes.

Under suboptimal conditions (e.g. suboptimal acidity in second electrolyte solution, suboptimal voltage $V_1$ or $V_2$, suboptimal temperature, or suboptimal first or second time period $t_1$ or $t_2$), pitting corrosion and/or amorphous material or particulate may or may not be observed. In some embodiments, pitting corrosion and/or amorphous material or particulate are substantially absent from the resulting surface.

FIG. 11 shows a process flow diagram for one embodiment of a method of forming metal oxide nanostructures. At block 710, a nickel titanium anode and at least one cathode are optionally provided. The anode can be an implantable medical device, including but not limited to a stent, containing a nickel titanium alloy. The anode can also be an orthopedic implant, such as a knee implant, bone screw, or bone staple, such as those used for hand and foot bone fragments osteotomy fixation and joint arthrodesis. The cathode can be platinum.

At block 720, the anode and cathode(s) are placed in electrical contact through a first electrolyte solution including about 99.2 vol % ethylene glycol (e.g. 99.2 ml) and about 0.8 vol % water (e.g. 0.8 ml), and about 0.18 wt % ammonium fluoride (e.g. 0.2 g). The temperature of the first electrolyte solution is maintained at about 30° C.

At block 730, a first voltage of about 25V is applied across the anode and cathode(s) through the first electrolyte solution for about 5 minutes.

At block 740, the first electrolyte solution is modified by the addition of hydroiodic acid, resulting in a second electrolyte solution including ethylene glycol (e.g. about 98.8 wt %), fluoride-bearing species (e.g. about 0.20 wt %), water (e.g. about 0.8 wt %), and hydroiodic acid (e.g. 0.06 mmol (8 ul) 57 wt % hydroiodic acid per 100 ml of first electrolyte). The organic solvent can be ethylene glycol. The fluoride-bearing species can be ammonium fluoride. The temperature of the second electrolyte solution can be maintained at about 30° C.

At block 750, a second voltage of about 25V is applied across the anode and cathode(s) through the second electrolyte solution for about 5 minutes.

Under suboptimal conditions (e.g. suboptimal acidity in second electrolyte solution, suboptimal voltage $V_1$ or $V_2$, suboptimal temperature, or suboptimal first or second time period $t_1$ or $t_2$), pitting corrosion and/or amorphous material or particulate may or may not be observed. In some embodiments, pitting corrosion and/or amorphous material or particulate are substantially absent from the resulting surface.

Figure 12:
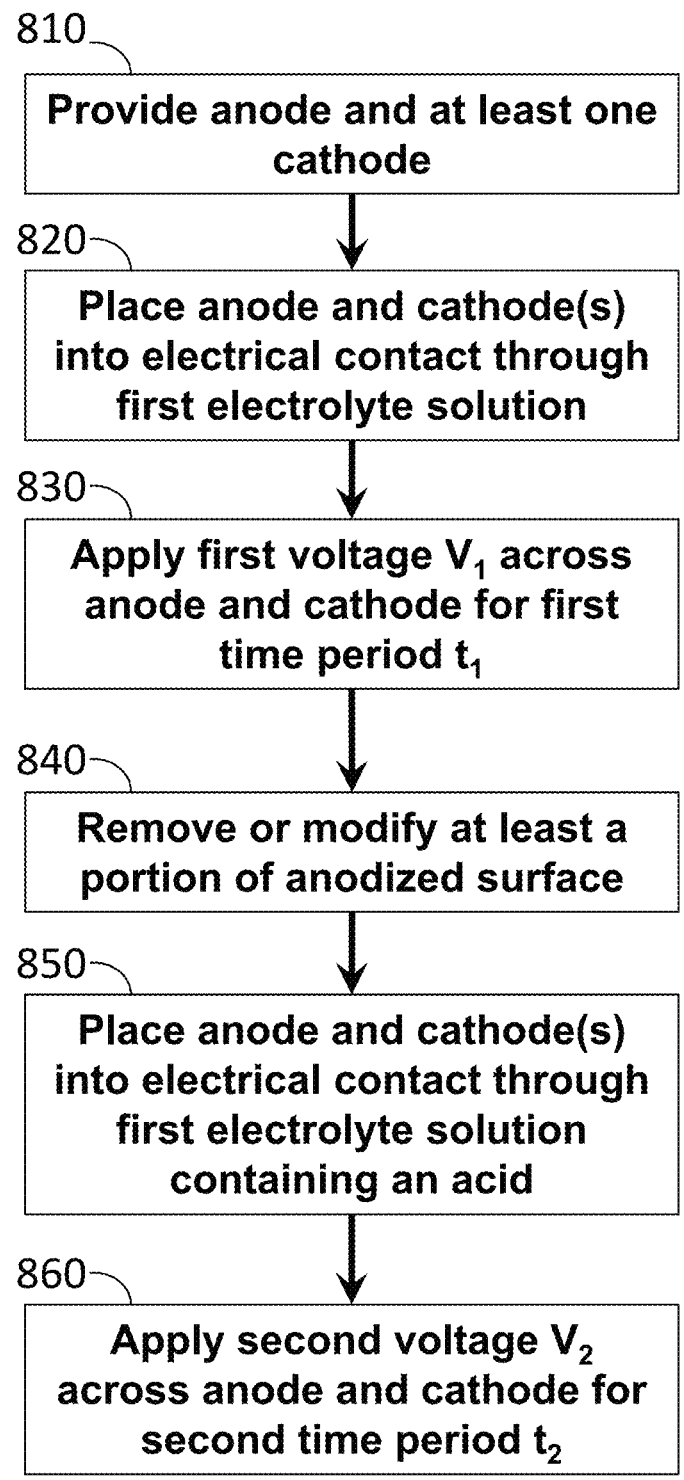
FIG. 12 shows a process flow diagram for another embodiment of a method of forming metal oxide nanostructures.

FIG. 12 shows a process flow diagram for one embodiment of a method of forming metal oxide nanostructures. At block 810, an anode and at least one cathode are optionally provided. In some embodiments, the anode contains an alloy of nickel and titanium. In some embodiments, the anode contains an alloy of nickel and titanium, with a ratio of nickel to titanium of approximately 1:1. In some embodiments, the anode can be an implantable medical device, including but not limited to a stent. The anode can also be an orthopedic implant, such as a knee implant, bone screw, or bone staple, such as those used for hand and foot bone fragments osteotomy fixation and joint arthrodesis. The at least one cathode(s) can be made from any suitable material, including but not limited to platinum, iron, stainless steel, or graphite. If more than one cathode is used, they can be positioned such that they are a similar distance from the anode, and optionally in a symmetrical fashion, and the setup can optionally include a reference electrode.

At block 820, the anode and cathode(s) are placed in electrical contact through a first electrolyte solution. The first electrolyte solution includes an organic solvent, a fluoride-bearing species, and an oxygen source. The organic solvent can be ethylene glycol. In some embodiments, the fluoride-bearing species can be ammonium fluoride. The oxygen source can be water, or it can be any other single oxygen donor compound, such as methanol. In some embodiments, the first electrolyte does not include an acid. In some embodiments, the first electrolyte solution includes about 99.2 vol % organic solvent and about 0.8 vol % water, and about 0.18 wt % fluoride-bearing species. The first electrolyte solution can be maintained at a relatively constant temperature. The temperature of the first electrolyte solution can be between about 10° and 50° Celsius. In some embodiments, the temperature of the first electrolyte solution is about 30° C.

At block 830, a first voltage $V_1$ is applied across the anode and cathode through the first electrolyte solution for a first time period $t_1$. The first voltage $V_1$ can be between about 10V and about 60V. In some embodiments, the first voltage $V_1$ is about 25V. In some embodiments, the first voltage applied across the anode and cathode is constant for the first time period $t_1$. In other embodiments, the first voltage applied across the anode and cathode varies over time throughout the first time period $t_1$, as for example when the anodization is run in a galvanostatic mode. The first time period $t_1$ can be between about 1 minute and about 120 minutes. In some embodiments, the first time period $t_1$ is approximately 5 minutes. In some embodiments, the first time period $t_1$ is less than 5 minutes. In other embodiments, the first time period is greater than 5 minutes, including about 6, 7, 8, 9, or 10 minutes. In some embodiments, the first time period is greater than 10 minutes and less than 60 minutes. In some embodiments, the first time period is greater than 60 minutes.

At block 840, at least a portion of the anodized surface (e.g. oxide material) of the anode is removed or modified. A portion of the anodized surface (e.g. oxide material) can be removed or modified by a variety of acceptable methods, including but not limited to etching, electrochemical anodization, and ultrasound. In other embodiments, a portion of the anodized surface (e.g. oxide material) can be removed or modified by cleaning it (e.g. ultrasonic cleaning, plasma cleaning), rinsing it (e.g. with water or other solvent), or annealing. In some embodiments, the oxide layer (e.g. nanotubes) formed during the first time period can be completely or partially removed from the substrate, leaving the resulting surface of the substrate characterized by a pattern of nanopores or nanopits.

At block 850, the anode and cathode(s) are placed in electrical contact through a second electrolyte solution. The second electrolyte solution includes an organic solvent, a fluoride-bearing species, an oxygen source, and an acid. The organic solvent can be ethylene glycol. In some embodiments, the fluoride-bearing species can be ammonium fluoride. The oxygen source can be water, or it can be any other single oxygen donor compound, such as methanol. The acid can be selected from the group consisting of $H_2SO_4$, HF, HCl, HBr, HI, $H_3PO_4$, $HNO_3$, formic acid, adipic acid, fumaric acid, tartaric acid, citric acid, oxalic acid, lactic acid, acetic acid, trifluoroacetic acid, and others. In some embodiments, the acid is sulfuric acid ($H_2SO_4$). In some embodiments, the acid is hydroiodic acid (HI). The second electrolyte solution includes greater than about 90 vol % organic solvent, about 0.8 vol % water, about 0.001-9.0 vol % acid, and fluoride-bearing species (wt % dependent on acid used in second electrolyte solution). The appropriate percentage of acid in the second electrolyte solution depends on many factors including the acid(s) used and the molecular weight and pKa of said acid(s). The second electrolyte solution can be maintained at a relatively constant temperature. The temperature of the second electrolyte solution can be between about 10° and 50° Celsius. In some embodiments, the temperature of the second electrolyte solution is about 30° C.

At block 860, a second voltage $V_2$ is applied across the anode and cathode through the second electrolyte solution for a second time period. In some embodiments, the second voltage is about 25V. In some embodiments, the second voltage $V_2$ is constant throughout the second time period $t_2$. In other embodiments, the second voltage $V_2$ varies throughout the second time period $t_2$. The second time period $t_2$ can be between about 1 minute and about 120 minutes. In some embodiments, the second time period $t_2$ is approximately 5 minutes. In some embodiments, the second time period $t_2$ is less than 5 minutes. In other embodiments, the second time period $t_2$ is greater than 5 minutes, including about 6, 7, 8, 9, or 10 minutes. In some embodiments, the second time period $t_2$ is greater than 10 minutes and less than 60 minutes. In some embodiments, the second time period $t_2$ is greater than 60 minutes.

Under suboptimal conditions (e.g. suboptimal acidity in second electrolyte solution, suboptimal voltage $V_1$ or $V_2$, suboptimal temperature, or suboptimal first or second time period $t_1$ or $t_2$), pitting corrosion and/or amorphous material or particulate may or may not be observed. In some embodiments, pitting corrosion and/or amorphous material or particulate are substantially absent from the resulting surface.

Figure 13:
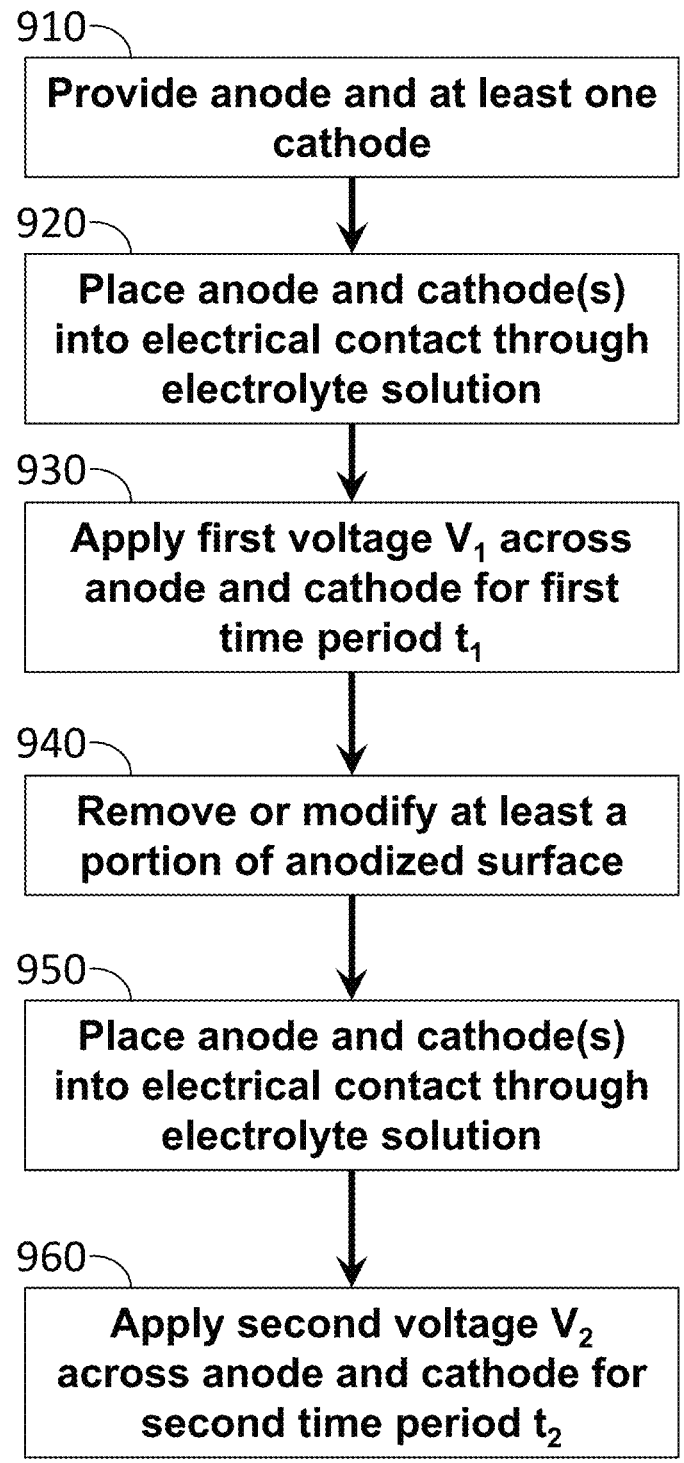
FIG. 13 shows a process flow diagram for another embodiment of a method of forming metal oxide nanostructures.

FIG. 13 shows a process flow diagram for one embodiment of a method of forming metal oxide nanostructures. At block 910, an anode and at least one cathode are optionally provided. In some embodiments, the anode contains an alloy of nickel and titanium. In some embodiments, the anode contains an alloy of nickel and titanium, with a ratio of nickel to titanium of approximately 1:1. In some embodiments, the anode can be an implantable medical device, including but not limited to a stent. The anode can also be an orthopedic implant, such as a knee implant, bone screw, or bone staple, such as those used for hand and foot bone fragments osteotomy fixation and joint arthrodesis. The at least one cathode(s) can be made from any suitable material, including but not limited to platinum, iron, stainless steel, or graphite. If more than one cathode is used, they can be positioned such that they are a similar distance from the anode, and optionally in a symmetrical fashion, and the setup can optionally include a reference electrode.

At block 920, the anode and cathode(s) are placed in electrical contact through an electrolyte solution. The electrolyte solution includes an organic solvent, a fluoride-bearing species, and an oxygen source. The organic solvent can be ethylene glycol. In some embodiments, the fluoride-bearing species can be ammonium fluoride. The oxygen source can be water, or it can be any other single oxygen donor compound, such as methanol. In some embodiments, the electrolyte does not include an acid. In some embodiments, the electrolyte solution includes about 99.2 vol % organic solvent and about 0.8 vol % water, and about 0.18 wt % fluoride-bearing species. The electrolyte solution can be maintained at a relatively constant temperature. The temperature of the electrolyte solution can be between about 10° and 50° Celsius. In some embodiments, the temperature of the electrolyte solution is about 30° C.

At block 930, a first voltage $V_1$ is applied across the anode and cathode through the electrolyte solution for a first time period $t_1$. The first voltage $V_1$ can be between about 10V and about 60V. In some embodiments, the first voltage $V_1$ is about 25V. In some embodiments, the first voltage applied across the anode and cathode is constant for the first time period $t_1$. In other embodiments, the first voltage applied across the anode and cathode varies over time throughout the first time period $t_1$, as for example when the anodization is run in a galvanostatic mode. The first time period $t_1$ can be between about 1 minute and about 120 minutes. In some embodiments, the first time period $t_1$ is approximately 5 minutes. In some embodiments, the first time period $t_1$ is less than 5 minutes. In other embodiments, the first time period is greater than 5 minutes, including about 6, 7, 8, 9, or 10 minutes. In some embodiments, the first time period is greater than 10 minutes and less than 60 minutes. In some embodiments, the first time period is greater than 60 minutes.

At block 940, at least a portion of the anodized surface (e.g. oxide material) of the anode is removed or modified. A portion of the anodized surface (e.g. oxide material) can be removed or modified by a variety of acceptable methods, including but not limited to etching, electrochemical anodization, and ultrasound. In other embodiments, a portion of the anodized surface (e.g. oxide material) can be removed or modified by cleaning it (e.g. ultrasonic cleaning, plasma cleaning), rinsing it (e.g. with water or other solvent), or annealing. In some embodiments, the oxide layer (e.g. nanotubes) formed during the first time period can be completely or partially removed from the substrate, leaving the resulting surface of the substrate characterized by a pattern of nanopores or nanopits.

At block 950, the anode and cathode(s) are again placed in electrical contact through the electrolyte solution. The electrolyte solution includes an organic solvent, a fluoride-bearing species, and an oxygen source. The organic solvent can be ethylene glycol. In some embodiments, the fluoride-bearing species can be ammonium fluoride. The oxygen source can be water, or it can be any other single oxygen donor compound, such as methanol. In some embodiments, the electrolyte does not include an acid. In some embodiments, the electrolyte solution includes about 99.2 vol % organic solvent and about 0.8 vol % water, and about 0.18 wt % fluoride-bearing species. The electrolyte solution can be maintained at a relatively constant temperature. The temperature of the electrolyte solution can be between about 10° and 50° Celsius. In some embodiments, the temperature of the electrolyte solution is about 30° C.

At block 960, a second voltage $V_2$ is applied across the anode and cathode through the second electrolyte solution for a second time period. In some embodiments, the second voltage is about 25V. In some embodiments, the second voltage $V_2$ is constant throughout the second time period $t_2$. In other embodiments, the second voltage $V_2$ varies throughout the second time period $t_2$. The second time period $t_2$ can be between about 1 minute and about 120 minutes. In some embodiments, the second time period $t_2$ is approximately 5 minutes. In some embodiments, the second time period $t_2$ is less than 5 minutes. In other embodiments, the second time period $t_2$ is greater than 5 minutes, including about 6, 7, 8, 9, or 10 minutes. In some embodiments, the second time period $t_2$ is greater than 10 minutes and less than 60 minutes. In some embodiments, the second time period $t_2$ is greater than 60 minutes.

Under suboptimal conditions (e.g. suboptimal acidity in second electrolyte solution, suboptimal voltage $V_1$ or $V_2$, suboptimal temperature, or suboptimal first or second time period $t_1$ or $t_2$), pitting corrosion and/or amorphous material or particulate may or may not be observed. In some embodiments, pitting corrosion and/or amorphous material or particulate are substantially absent from the resulting surface.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and/or advantages. These also include embodiments in which the components and/or steps are arranged and/or ordered differently.

Example 1. Forming Metal Oxide Nanostructures on Nickel Titanium Foil

An electrolyte solution was prepared containing 0.8 vol % deionized water ($H_2O$) (e.g. 0.8 ml), 0.18 wt % ammonium fluoride ($NH_4F$) (e.g. 0.2 g) (Sigma Aldrich), and 99.2 vol % ethylene glycol (e.g. 99.2 ml) (Sigma Aldrich). The electrolyte solution was brought to and maintained at 30° C.

50 mm×50 mm×0.127 mm (W×H×D) nitinol foil (Alfa Aesar) was cut into 6 mm×6 mm×0.127 mm (W×H×D) and 8 mm×8 mm×0.127 mm (W×H×D) coupons and then successively ultrasonically cleaned with acetone, ethanol, and deionized water for 5 minutes each. The coupons were then kept in 70% ethanol until further use. Prior to anodization, the coupons were rinsed in deionized water and air dried.

For anodization, the cleaned nitinol coupons were then secured such that only one face of the coupon was exposed to the reaction conditions. The secured nitinol coupons were positioned approximately 2 cm from a platinum cathode (Sigma Aldrich). The platinum cathode had the same surface area as the nitinol coupon being anodized (e.g. 6 mm×6 mm or 8 mm×8 mm).

Figure 14:
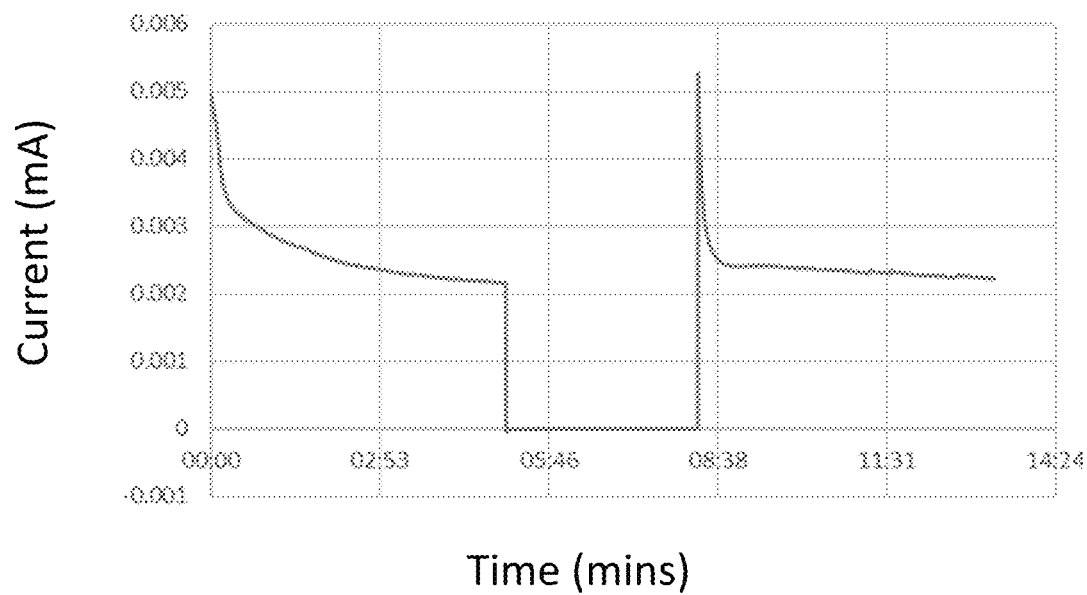
FIG. 14 shows a representative current profile resulting from performing the method described in Example 1.

A power supply (Agilent Technologies) provided a constant voltage of 25V between the anode (nitinol coupon) and platinum cathode for 5 minutes. During this time, the current was variable as monitored by a digital multimeter (Agilent Technologies) connected to a desktop computer running BenchVue 3.1 (Keysight Technologies). A representative current profile (including the current from the second time period) is shown in FIG. 14.

After the first 5 minute anodization, 0.06 mmol (8 ul) 57 wt % hydroiodic acid (Sigma Aldrich) was added to the electrolyte solution from the first step. The electrolyte solution continued to be maintained at 30° C. The power supply then provided a constant voltage of 25V between the anode (nitinol coupon) and cathode for another 5 minutes. During this second 5-minute run, the electrolyte solution was stirred using magnetic PTFE-coated stir bar at 300 rpm.

Figure 15:
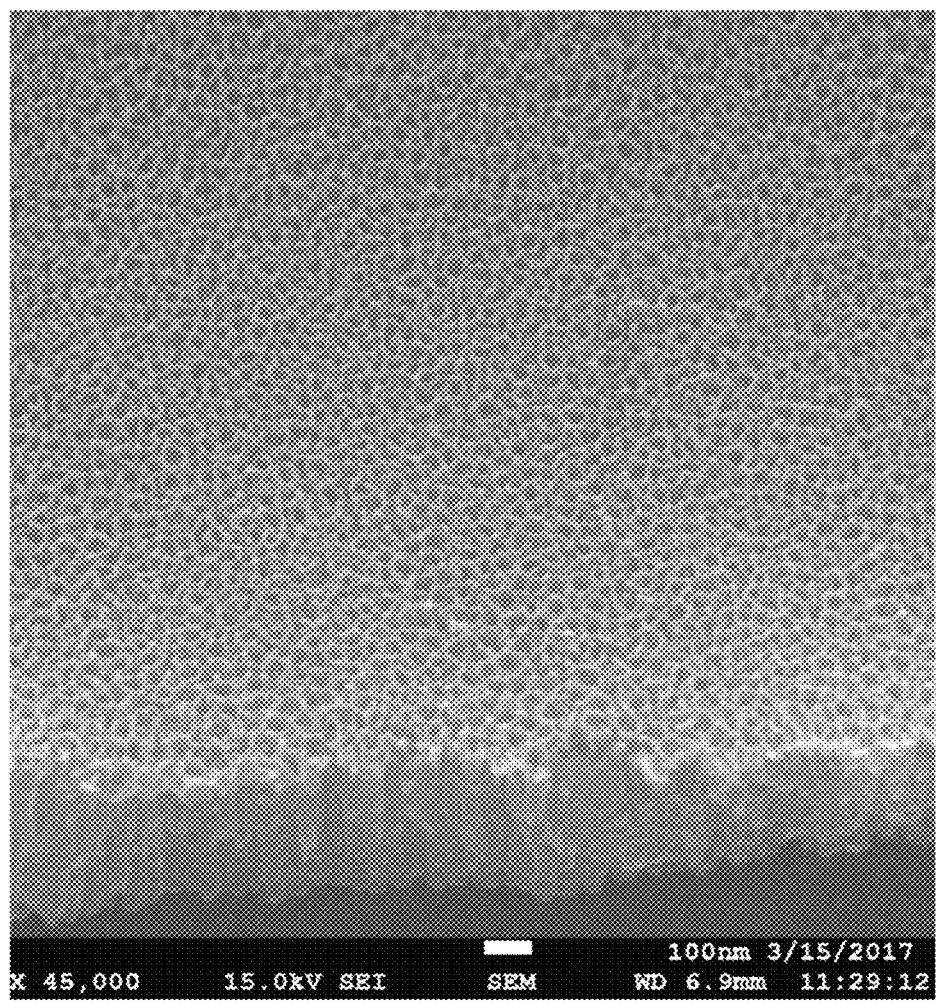
FIG. 15 shows a representative scanning electron microscope (SEM) image of a metal oxide nanostructured surface resulting from the method described in Example 1.

After the second 5-minute run, the coupons were rinsed in deionized water and kept in 70% ethanol until further use or evaluation. The coupons were then imaged using scanning electron microscopy (SEM) (representative image shown in FIG. 15).

Example 2. Forming Metal Oxide Nanostructures on Nickel Titanium Foil

An electrolyte solution was prepared containing 0.8 vol % deionized water ($H_2O$) (e.g. 0.8 ml), 0.18 wt % ammonium fluoride ($NH_4F$) (e.g. 0.2 g) (Sigma Aldrich), and 99.2 vol % ethylene glycol (e.g. 99.2 ml) (Sigma Aldrich). The electrolyte solution was brought to and maintained at 30° C.

50 mm×50 mm×0.127 mm (W×H×D) nitinol foil (Alfa Aesar) was cut into 6 mm×6 mm×0.127 mm (W×H×D) and 8 mm×8 mm×0.127 mm (W×H×D) coupons and then successively ultrasonically cleaned with acetone, ethanol, and deionized water for 5 minutes each. The coupons were then kept in 70% ethanol until further use. Prior to anodization, the coupons were rinsed in deionized water and air dried.

For anodization, the cleaned nitinol coupons were then secured such that only one face of the coupon was exposed to the reaction conditions. The secured nitinol coupons were positioned approximately 2 cm from a platinum cathode (Sigma Aldrich). The platinum cathode had the same surface area as the nitinol coupon being anodized (e.g. 6 mm×6 mm or 8 mm×8 mm).

A power supply (Agilent Technologies) provided a constant voltage of 25V between the anode (nitinol coupon) and platinum cathode for 5 minutes. During this time, the current was variable as monitored by a digital multimeter (Agilent Technologies) connected to a desktop computer running BenchVue 3.1 (Keysight Technologies).

After the first 5 minute anodization, 3 mmol (163.2 ul) 95-98 wt % sulfuric acid (VWR) was added to the electrolyte solution from the first step. The electrolyte solution continued to be maintained at 30° C. The power supply then provided a constant voltage of 25V between the anode (nitinol coupon) and cathode for another 5 minutes. During this second 5-minute run, the electrolyte solution was stirred using magnetic PTFE-coated stir bar at 300 rpm.

Figure 16:
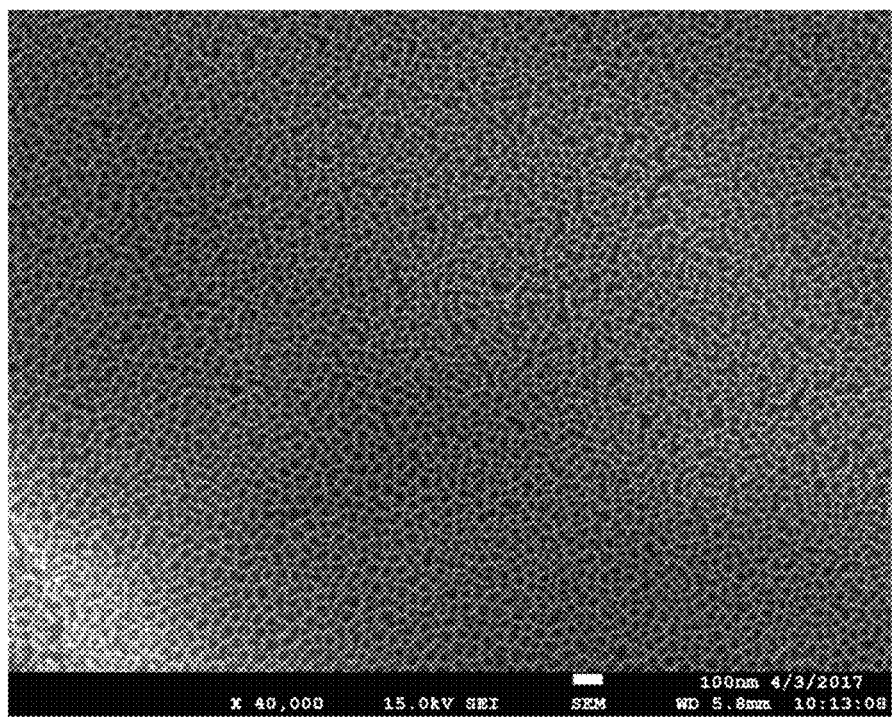
FIG. 16 shows a representative SEM image of a metal oxide nanostructured surface resulting from the method described in Example 2.

After the second 5 minute run, the coupons were rinsed in deionized water and kept in 70% ethanol until further use or evaluation. Some of the coupons were then imaged using SEM (representative image shown in FIG. 16).

Example 3. Forming Metal Oxide Nanostructures on Nickel Titanium Foil

An electrolyte solution was prepared containing 0.8 vol % deionized water ($H_2O$) (e.g. 0.8 ml), 0.18 wt % ammonium fluoride ($NH_4F$) (e.g. 0.2 g) (Sigma Aldrich), and 99.2 vol % ethylene glycol (e.g. 99.2 ml) (Sigma Aldrich). The electrolyte solution was brought to and maintained at 22° C.

50 mm×50 mm×0.127 mm (W×H×D) nitinol foil (Alfa Aesar) was cut into 6 mm×6 mm×0.127 mm (W×H×D) and then successively ultrasonically cleaned with acetone, ethanol, and deionized water for 5 minutes each. The coupons were then kept in 70% ethanol until further use. Prior to anodization, the coupons were rinsed in deionized water and air dried.

For anodization, the cleaned nitinol coupons were then secured such that only one face of the coupon was exposed to the reaction conditions. The secured nitinol coupons were positioned approximately 2 cm from a platinum cathode (Sigma Aldrich). The platinum cathode had the same surface area as the nitinol coupon being anodized (e.g. 6 mm×6 mm).

A power supply (Agilent Technologies) provided a constant voltage of 25V between the anode (nitinol coupon) and platinum cathode for 5 minutes. During this time, the current was variable as monitored by a digital multimeter (Agilent Technologies) connected to a desktop computer running BenchVue.

After the first 5 minute anodization, 0.06 mmol (8 ul) 57 wt % hydroiodic acid (Sigma Aldrich) was added to the electrolyte solution from the first step. The electrolyte solution continued to be maintained at 22° C. The power supply then provided a constant voltage of 25V between the anode (nitinol coupon) and cathode for another 7 minutes. During this second 7-minute run, the electrolyte solution was stirred using magnetic PTFE-coated stir bar at 300 rpm.

After the second 5-minute run, the coupons were rinsed in deionized water and kept in 70% ethanol until further use or evaluation.

Example 4. Determining the Elemental Composition of the Surface of the Oxide Nanostructures 50 mm×50 mm×0.127 mm (W×H×D) nitinol foil (Alfa Aesar) was cut into 6 mm×6 mm×0.127 mm (W×H×D) coupons. One of these 6 mm×6 mm×0.127 mm (W×H×D) nitinol foil coupons (Alfa Aesar) was then prepared as described in Example 1, and three discrete spots on this coupon were quantified using standard x-ray photoelectron spectroscopy (XPS) to determine the relative nickel, titanium carbon, and oxygen content at the surface of the anodized nitinol coupon. The results found by XPS are shown in Table 1.

TABLE 1

| Sample | Relative Atomic Concentration (%) | | | |
|---|---|---|---|---|
| | Ni | Ti | C | O |
| 1 | 2.3 | 39.5 | 30 | 28.2 |
| 2 | 2.5 | 41.1 | 26.3 | 30.1 |
| 3 | 2.1 | 41.3 | 27.1 | 29.5 |

Example 5. Endothelial Response to Oxide Nanostructures

Human aortic endothelial cells (HAECs) (passage 4) were cultured in wells with standard techniques on 500 um thick 4 mg/ml collagen substrate (rat tail Corning #354236) at a seeding density of 10,000 cells per $cm^2$ until confluent (approx. 2-3 days).

Figure 17:
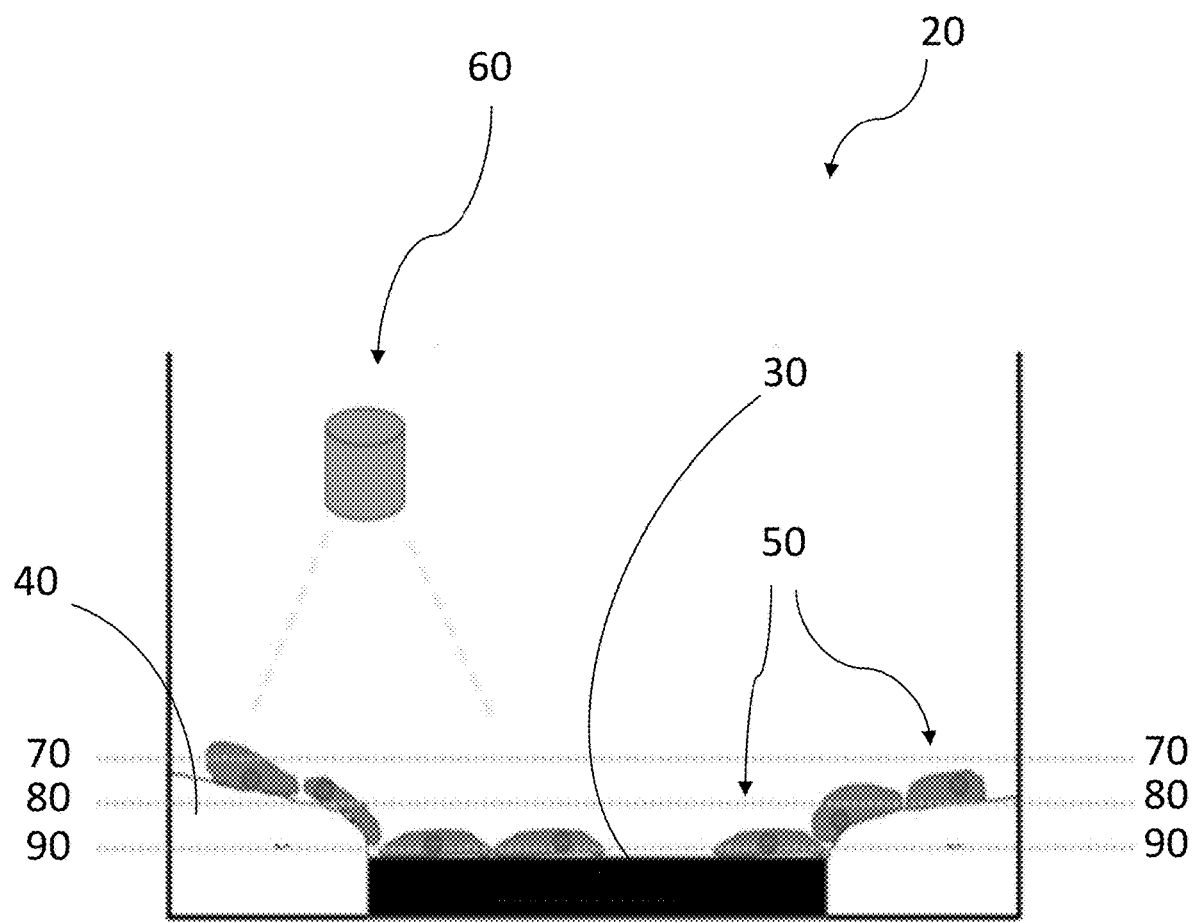
FIG. 17 shows a schematic representation of part of the experimental setup described in Example 5.
Figure 18A:
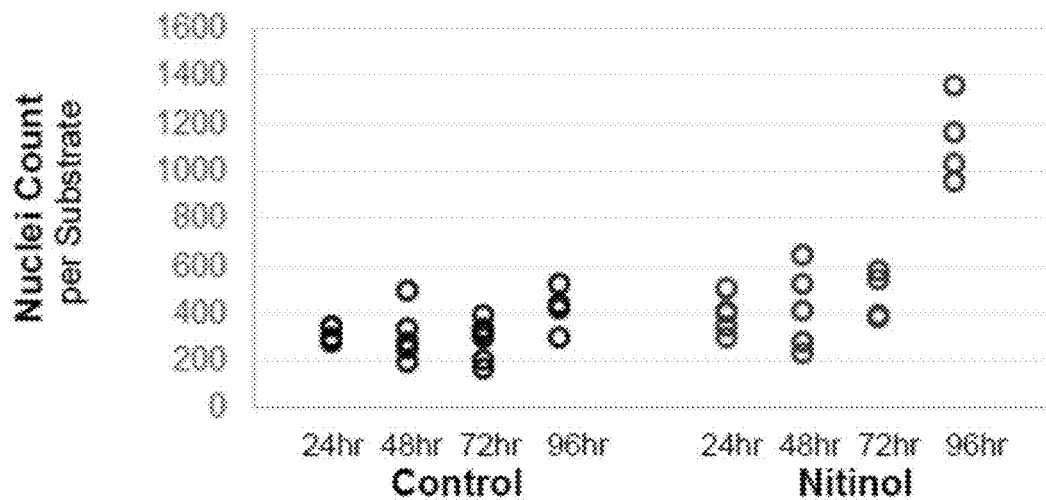
FIGS. 18A-D show plots of the data resulting from the experiments described in Example 5.
Figure 18B:
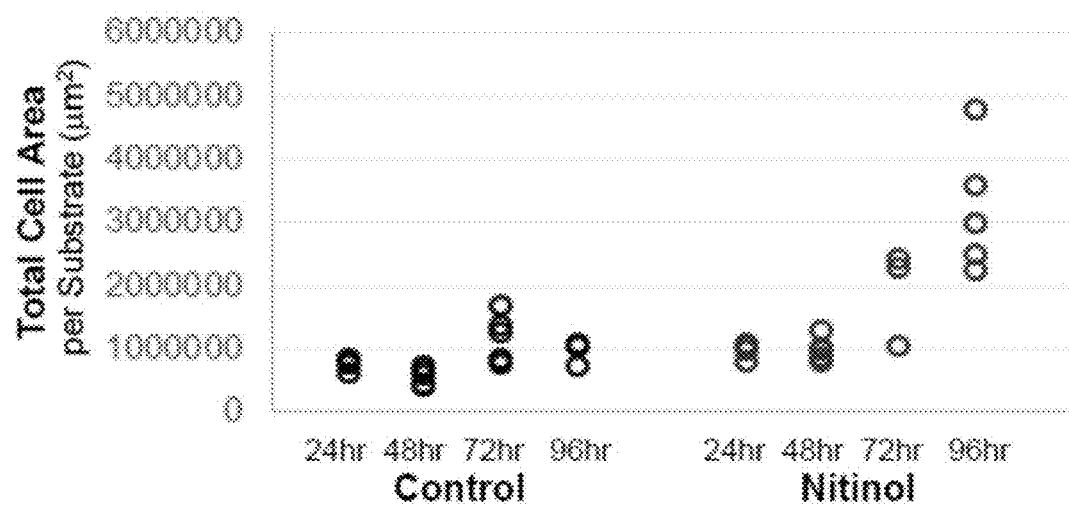
Figure 18C:
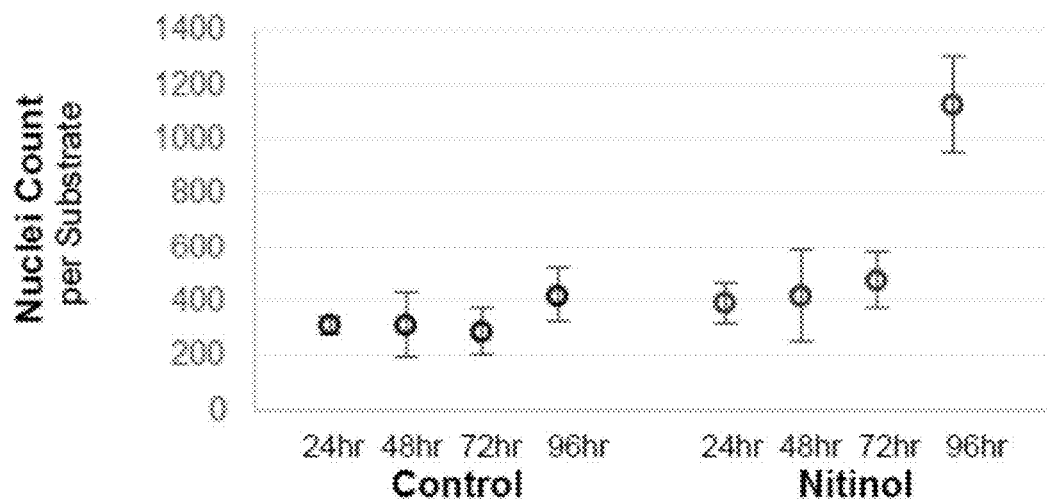
Figure 18D:
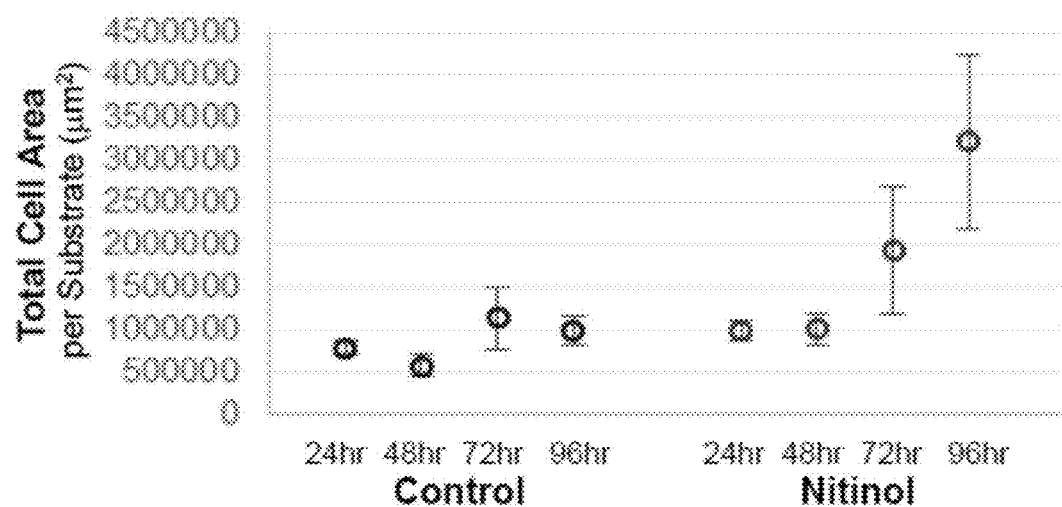
Figure 19A:
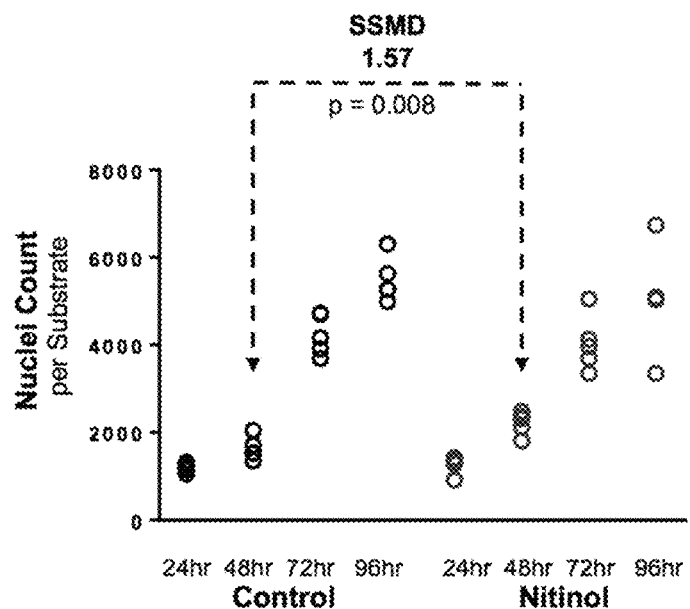
FIGS. 19A-D show plots of the data resulting from the experiments described in Example 6.
Figure 19B:
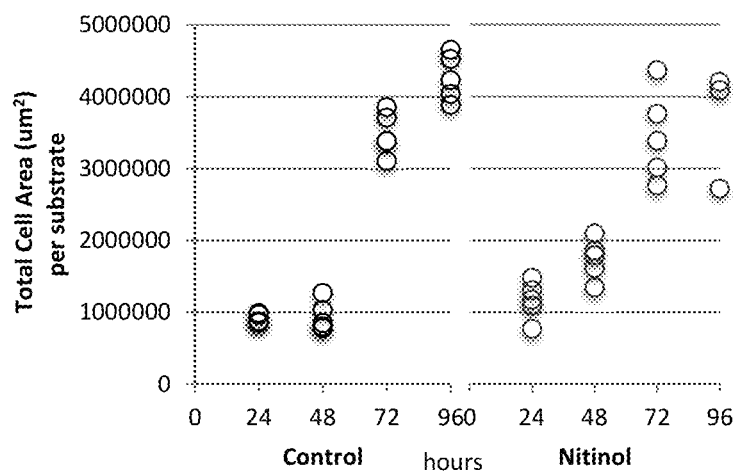
Figure 19C:
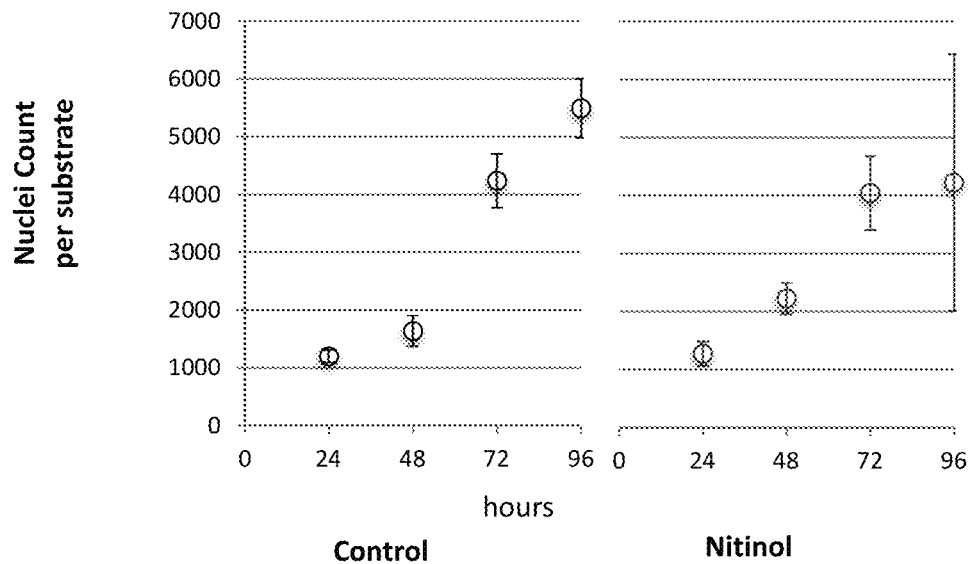
Figure 19D:
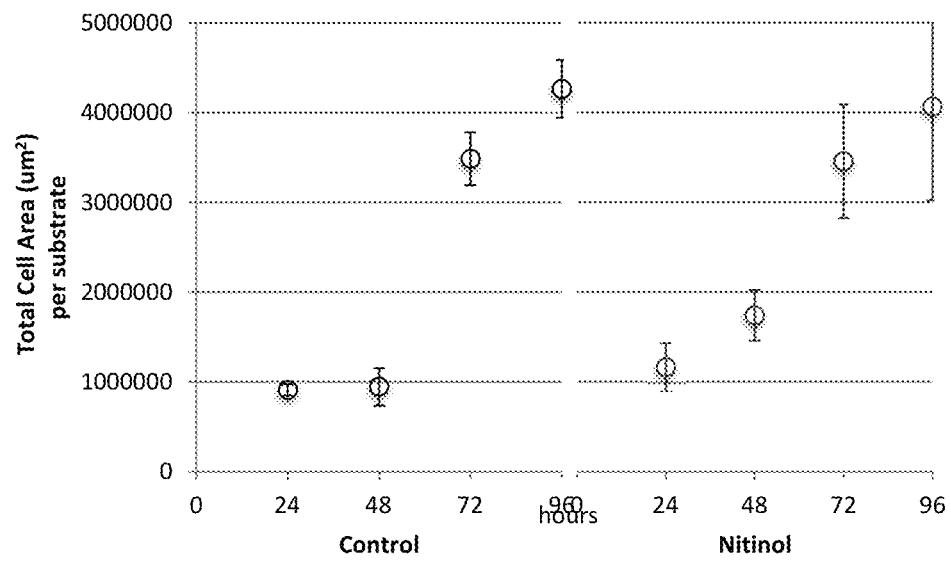

FIG. 17 is a schematic representation of the well setup 20. As represented in FIG. 17, an insert 30 (e.g. nanostructured nitinol coupon, control coupon) was pushed into the collagen substrate 40 with HAECs 50, allowing the HAECs 50 to migrate onto the surface of the insert 30. The well setup was then imaged along various focal planes 70, 80, and 90

Twenty 6 mm×6 mm×0.127 mm (W×H×D) nitinol foil coupons (Alfa Aesar) prepared as described in Example 3 above were cleaned three times each with 1 mL sterile water. The coupons were then inserted into 20 wells (one coupon per well) with confluent HAEC layers, as shown in FIG. 17, with the oxide nanostructures facing up (away from the confluent HAEC layer). 20 untreated 6 mm×6 mm×0.127 mm (W×H×D) nitinol coupons (control) were then cleaned three times each with 1 mL sterile water, and then inserted into 20 wells (one coupon per well) with confluent HAEC layers, as shown in FIG. 17, with a clean native oxide layer facing up.

At time periods of 24 hours, 48 hours, 72 hours, and 96 hours post-coupon insertion, wells were stained with Cell-Tracker Green for 30 minutes, fixed in 4% PFA, and counter-stained with Hoechst 33342, a nuclear stain, for 20 minutes (five nanostructured coupons and 5 control coupons per time point). The wells were then imaged with Thermo-Scientific CX7 automated quantitative fluorescence microscope. Measurements were made to determine cell count, average cell area, and cell morphology (e.g. P2A, LWR). For purposes of these measurements, only cell nuclei associated with CellTracker Green were counted as live cells. Compared to the control coupons, the coupons with the oxide nanostructures were found to have about 3 times more live cells at 96 hours (Tables 2 & 3; FIGS. 18A-D).

TABLE 2

| Sample | Total Nuclei Count |
| --- | --- |
| Control #1 | 529.92 |
| Control #2 | 443.76 |
| Control #3 | 298.41 |
| Control #4 | 425.88 |
| Mean Control | 424.49 |
| Nanostructured Nitinol #1 | 961.61 |
| Nanostructured Nitinol #2 | 1163.34 |
| Nanostructured Nitinol #3 | 2313 |
| Nanostructured Nitinol #4 | 1364.52 |
| Nanostructured Nitinol #5 | 1035 |
| Mean Nanostructured Nitinol | 1367.50 |

TABLE 3

| Sample | Total Cell Area ($\mu m^2$) |
| --- | --- |
| Control #1 | 1,056,118.14 |
| Control #2 | 1,108,398.96 |
| Control #3 | 737,071.23 |
| Control #4 | 1,050,531.3 |
| Mean Control | 98,8029.91 |
| Nanostructured Nitinol #1 | 2,242,548.6 |
| Nanostructured Nitinol #2 | 3,577,368.85 |
| Nanostructured Nitinol #3 | 4,799,538 |
| Nanostructured Nitinol #4 | 2,982,154.35 |
| Nanostructured Nitinol #5 | 2,487,768 |
| Mean Nanostructured Nitinol | 3,217,875.56 |

Example 6. Smooth Muscle Cell Response to Oxide Nanostructures

Human aortic smooth muscle cells (HASMs) (passage 3) were cultured in wells with standard techniques on 500 um thick 4 mg/ml collagen substrate (rat tail Corning #354236) at a seeding density of approx. 120,481 cells per cm² until confluent (approx. 24 hours).

FIG. 17 is a schematic representation of the well setup 20. As represented in FIG. 17, an insert 30 (e.g. nanostructured nitinol coupon, control coupon) was pushed into the collagen substrate 40 with HASMs 50, allowing the HASMs 50 to migrate onto the surface of the insert 30. The well setup was then imaged along various focal planes 70, 80, and 90

Twenty 6 mm×6 mm×0.127 mm (W×H×D) nitinol foil coupons (Alfa Aesar) prepared as described in Example 3 above were cleaned three times each with 1 mL sterile PBS. The coupons were then inserted into 20 wells (one coupon per well) with confluent HASM layers, as shown in FIG. 17, with the oxide nanostructures facing up (away from the confluent HAEC layer). 20 untreated 6 mm×6 mm×0.127 mm (W×H×D) nitinol coupons (control) were then cleaned three times each with 1 mL sterile PBS, and then inserted into 20 wells (one coupon per well) with confluent HASM layers, as shown in FIG. 17, with a clean native oxide layer facing up.

At time periods of 24 hours, 48 hours, 72 hours, and 96 hours post-coupon insertion, wells were stained with Cell-Tracker Green for 30 minutes, fixed in 4% PFA, and counter-stained with Hoechst 33342, a nuclear stain, for 20 minutes (five nanostructured coupons and 5 control coupons per time point). The wells were then imaged with Thermo-Scientific CX7 automated quantitative fluorescence microscope. Measurements were made to determine cell count, average cell area, and cell morphology (e.g. P2A, LWR). For purposes of these measurements, only cell nuclei associated with CellTracker Green were counted as live cells. No statistically significant differences were observed in cell count or cell area after 96 hours (Tables 4 & 5, FIGS. 19A-D).

TABLE 4

| Sample | Total Nuclei Count |
| --- | --- |
| Control #1 | 5267 |
| Control #2 | 5633 |
| Control #3 | 6302 |
| Control #4 | 4987 |
| Control #5 | 5267 |
| Mean Control | 5491.2 |
| Nanostructured Nitinol #1 | 3347 |
| Nanostructured Nitinol #2 | 5092 |
| Nanostructured Nitinol #3 | 5037 |
| Nanostructured Nitinol #4 | 6735 |
| Mean Nanostructured Nitinol | 5052.75 |

TABLE 5

| Sample | Total Cell Area ($\mu m^2$) |
| --- | --- |
| Control #1 | 4,037,261 |
| Control #2 | 4,525,214 |
| Control #3 | 4,652,515 |
| Control #4 | 3,887,017 |
| Control #5 | 4,230,718 |
| Mean Control | 4,266,544.95 |
| Nanostructured Nitinol #1 | 2,717,597 |
| Nanostructured Nitinol #2 | 4,085,923 |
| Nanostructured Nitinol #3 | 4,202,671 |
| Nanostructured Nitinol #4 | 5,264,615 |
| Mean Nanostructured Nitinol | 4,067,701 |

Example 7. Forming Metal Oxide Nanostructures on Nickel Titanium Foil

An electrolyte solution was prepared containing 0.8 vol % deionized water ($H_2O$) (e.g. 0.8 ml), 0.18 wt % ammonium fluoride ($NH_4F$) (e.g. 0.2 g) (Sigma Aldrich), and 99.2 vol % ethylene glycol (e.g. 99.2 ml) (Sigma Aldrich). The electrolyte solution was brought to and maintained at 30° C.

50 mm×50 mm×0.127 mm (W×H×D) nitinol foil (Alfa Aesar) was cut into 6 mm×6 mm×0.127 mm (W×H×D) and 8 mm×8 mm×0.127 mm (W×H×D) coupons and then successively ultrasonically cleaned with acetone, ethanol, and deionized water for 5 minutes each. The coupons were then kept in 70% ethanol until further use. Prior to anodization, the coupons were rinsed in deionized water and air dried.

For anodization, the cleaned nitinol coupons were then secured such that only one face of the coupon was exposed to the reaction conditions. The secured nitinol coupons were positioned approximately 2 cm from a platinum cathode (Sigma Aldrich). The platinum cathode had the same surface area as the nitinol coupon being anodized (e.g. 6 mm×6 mm or 8 mm×8 mm).

Figure 20:
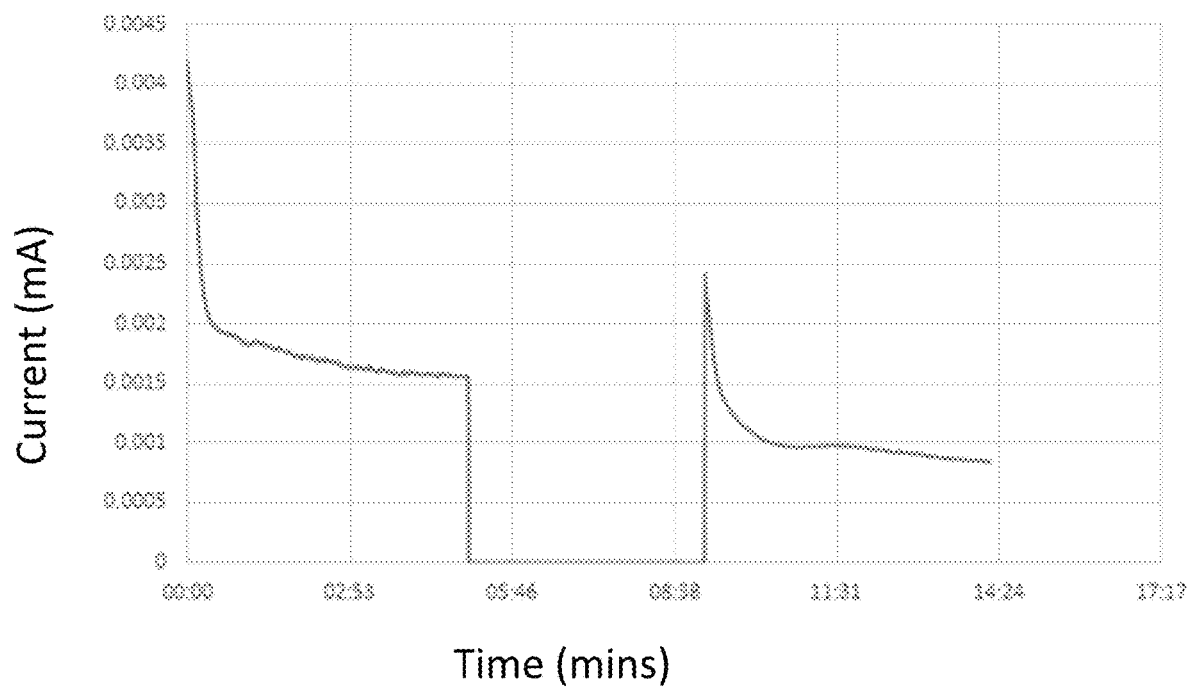
FIG. 20 shows a representative current profile resulting from performing the method described in Example 7.

A power supply (Agilent Technologies) provided a constant voltage of 25V between the anode (nitinol coupon) and platinum cathode for 5 minutes. During this time, the current was variable as monitored by a digital multimeter (Agilent Technologies) connected to a desktop computer running BenchVue 3.1 (Keysight Technologies). A representative current profile (including the current from the second time period) is shown in FIG. 20.

After the first 5 minute anodization, 56 mmol (10.8 g) citric acid (Sigma Aldrich) was added to the electrolyte solution from the first step. The electrolyte solution continued to be maintained at 30° C. The power supply then provided a constant voltage of 25V between the anode (nitinol coupon) and cathode for another 5 minutes. During this second 5-minute run, the electrolyte solution was stirred using magnetic PTFE-coated stir bar at 300 rpm.

Figure 21:
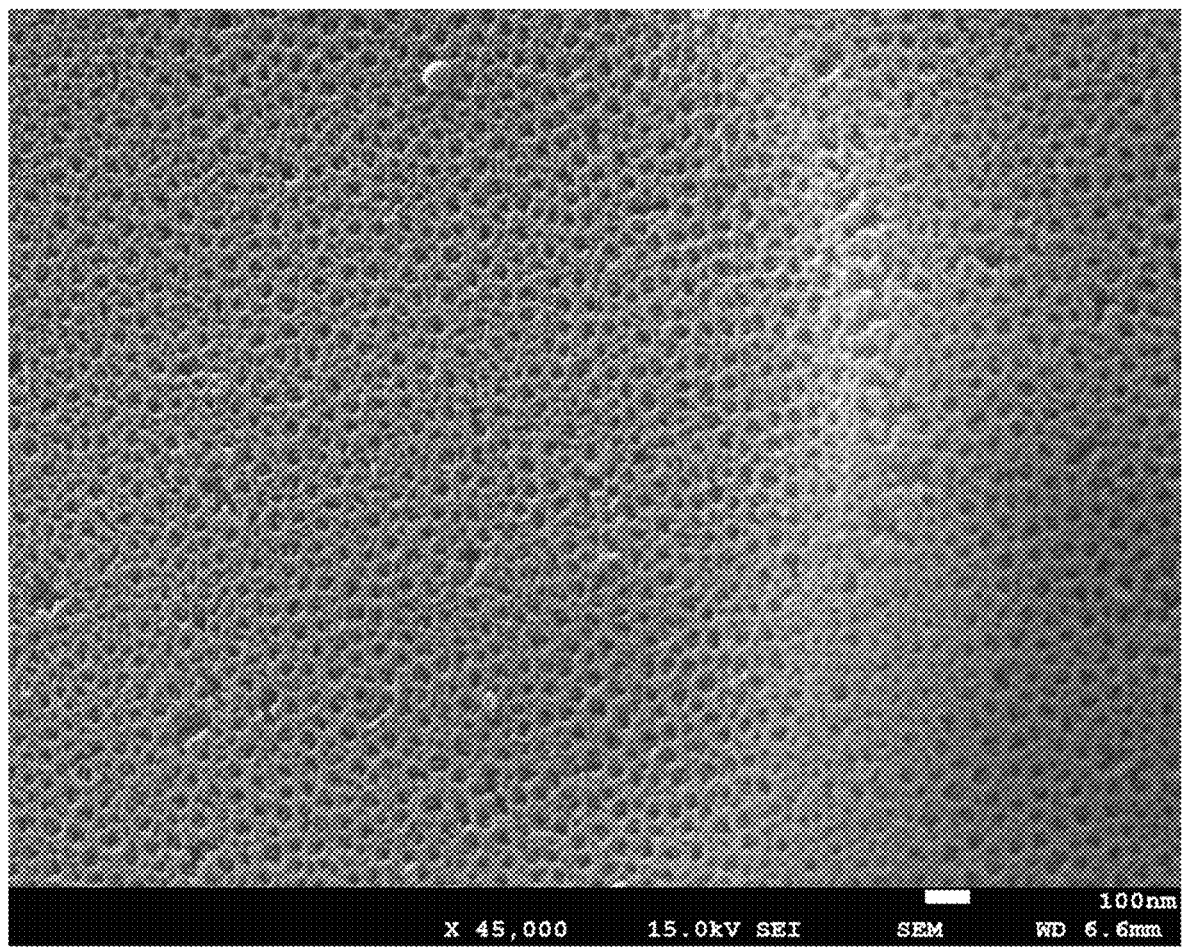
FIG. 21 shows a representative SEM image of a metal oxide nanostructured surface resulting from the method described in Example 7.

After the second 5-minute run, the coupons were rinsed in deionized water and kept in 70% ethanol until further use or evaluation. The coupons were then imaged using SEM (representative image shown in FIG. 21).

Example 8. Forming Metal Oxide Nanostructures on Nickel Titanium Foil

An electrolyte solution was prepared containing 0.8 vol % deionized water ($H_2O$) (e.g. 0.8 ml), 0.18 wt % ammonium fluoride ($NH_4F$) (e.g. 0.2 g) (Sigma Aldrich), and 99.2 vol % ethylene glycol (e.g. 99.2 ml) (Sigma Aldrich). The electrolyte solution was brought to and maintained at 30° C.

50 mm×50 mm×0.127 mm (W×H×D) nitinol foil (Alfa Aesar) was cut into 6 mm×6 mm×0.127 mm (W×H×D) and 8 mm×8 mm×0.127 mm (W×H×D) coupons and then successively ultrasonically cleaned with acetone, ethanol, and deionized water for 5 minutes each. The coupons were then kept in 70% ethanol until further use. Prior to anodization, the coupons were rinsed in deionized water and air dried.

For anodization, the cleaned nitinol coupons were then secured such that only one face of the coupon was exposed to the reaction conditions. The secured nitinol coupons were positioned approximately 2 cm from a platinum cathode (Sigma Aldrich). The platinum cathode had the same surface area as the nitinol coupon being anodized (e.g. 6 mm×6 mm or 8 mm×8 mm).

Figure 22:
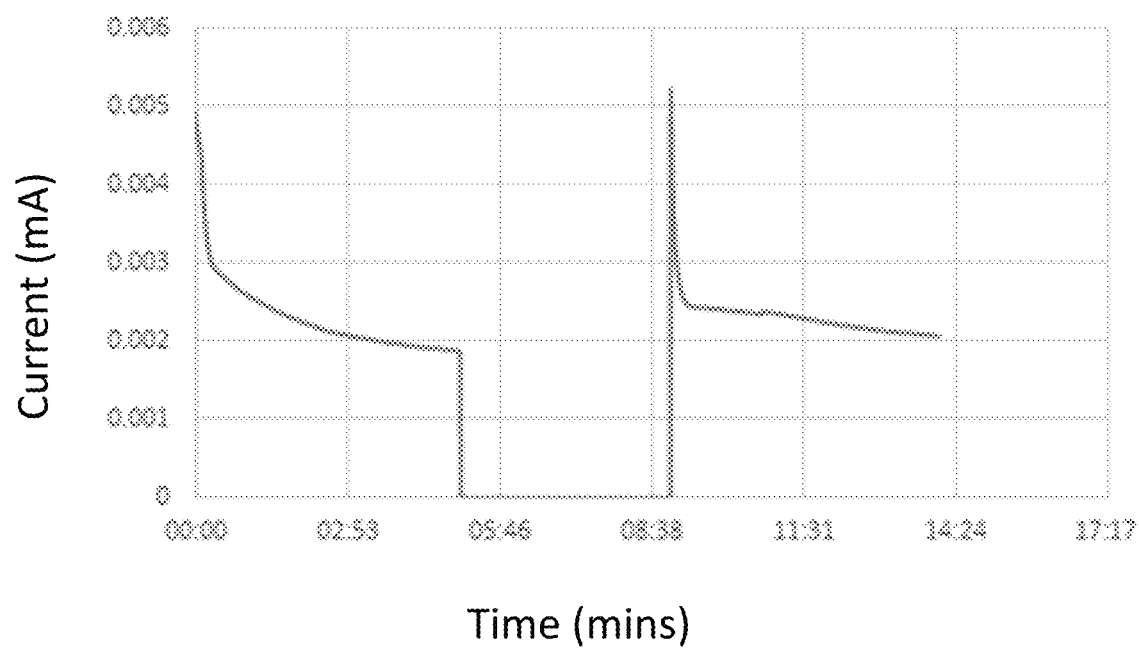
FIG. 22 shows a representative current profile resulting from performing the method described in Example 8.

A power supply (Agilent Technologies) provided a constant voltage of 25V between the anode (nitinol coupon) and platinum cathode for 5 minutes. During this time, the current was variable as monitored by a digital multimeter (Agilent Technologies) connected to a desktop computer running BenchVue 3.1 (Keysight Technologies). A representative current profile (including the current from the second time period) is shown in FIG. 22.

After the first 5 minute anodization, 1.4 mmol (0.1162 ml) lactic acid (90%, Sigma Aldrich) was added to the electrolyte solution from the first step. The electrolyte solution continued to be maintained at 30° C. The power supply then provided a constant voltage of 25V between the anode (nitinol coupon) and cathode for another 5 minutes. During this second 5-minute run, the electrolyte solution was stirred using magnetic PTFE-coated stir bar at 300 rpm.

Figure 23:
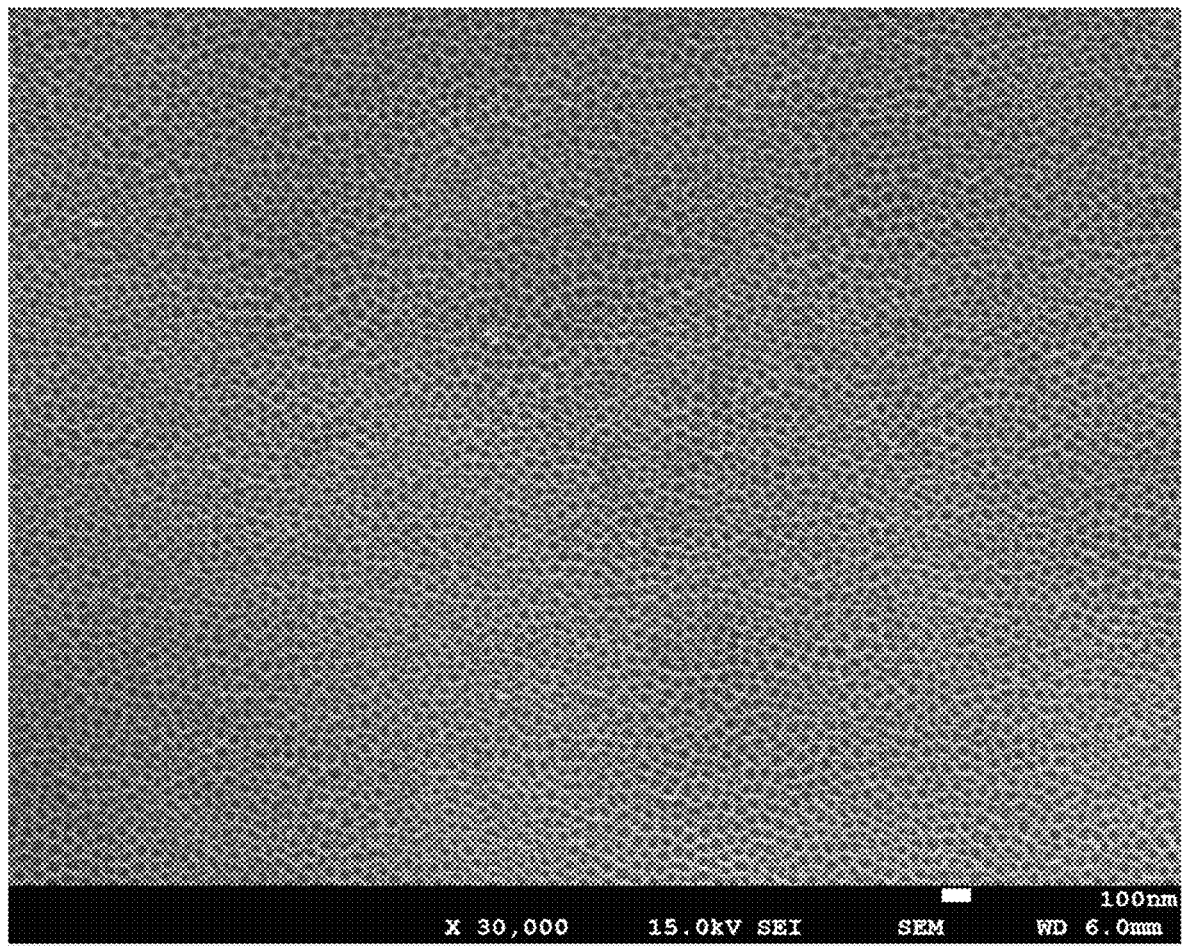
FIG. 23 shows a representative SEM image of a metal oxide nanostructured surface resulting from the method described in Example 8.

After the second 5-minute run, the coupons were rinsed in deionized water and kept in 70% ethanol until further use or evaluation. The coupons were then imaged using SEM (representative image shown in FIG. 23).

Additional Embodiments

In some embodiments, a metal oxide nanostructure formed on the surface of a substrate is provided, the metal oxide nanostructure comprising a first layer comprising a plurality of tubular structures and a second layer comprising a lattice structure, wherein the first layer is situated between the substrate and the second layer.

Some embodiments include the metal oxide nanostructure of any one or more of the preceding embodiments, wherein the substrate comprises an alloy of nickel and titanium.

Some embodiments include the metal oxide nanostructure of any one or more of the preceding embodiments, wherein the tubular structures comprise titanium oxide and nickel oxide in a ratio greater than or equal to 1:1.

Some embodiments include the metal oxide nanostructure of any one or more of the preceding embodiments, wherein the plurality of tubular structures are aligned generally perpendicular to the substrate and generally parallel to one another.

Some embodiments include the metal oxide nanostructure of any one or more of the preceding embodiments, wherein the plurality of tubular structures each have an outer surface, and wherein the outer surface of each of the plurality of tubular structures are in contact with the outer surfaces of each of the adjacent tubular structures.

Some embodiments include the metal oxide nanostructure of any one or more of the preceding embodiments, wherein the lattice comprises titanium oxide and nickel oxide.

Some embodiments include the metal oxide nanostructure of any one or more of the preceding embodiments, wherein the ratio of titanium oxide to nickel oxide on the distal surface of the lattice is greater than or equal to 10:1.

Some embodiments include the metal oxide nanostructure of any one or more of the preceding embodiments, wherein the substrate is an implantable medical device.

Some embodiments include the metal oxide nanostructure of any one or more of the preceding embodiments, wherein the substrate is a stent.

Some embodiments include the metal oxide nanostructure of any one or more of the preceding embodiments, wherein first and second layers are formed on a surface of the substrate using electrochemical anodization.

In some embodiments, a biocompatible surface formed on the surface of a stent is provided, the biocompatible surface comprising a first layer comprising a plurality of tubular structures aligned generally perpendicular to the surface of the stent and a second layer comprising a metal oxide lattice defining openings therein, wherein the first layer is situated between the surface of the implantable medical device and the second layer, the plurality of tubular structures each have an outer surface, the outer surface of each of the plurality of tubular structures are in contact with the outer surfaces of each of the adjacent tubular structures, and a distal surface of the metal oxide lattice comprises titanium oxide and nickel oxide, with the ratio of titanium oxide to nickel oxide being greater than or equal to 10:1.

Some embodiments include the biocompatible surface of any one or more of the preceding embodiments, wherein the surface promotes the growth of human aortic endothelial cells at an interface between the stent and an artery.

Some embodiments include the biocompatible surface of any one or more of the preceding embodiments, wherein the surface inhibits the growth of smooth muscle cells at an interface between the stent and an artery.

In some embodiments, a method of forming a metal oxide nanostructure is provided, the method comprising placing an anode and at least one cathode in electrical contact through a first electrolyte solution comprising an organic solvent, a fluoride-bearing species, and water, applying a first voltage across the anode and cathode through the first electrolyte solution for a first time period, modifying or replacing the first electrolyte solution resulting in a second electrolyte solution comprising an organic solvent, a fluoride-bearing species, water, and an acid, and applying a second voltage across the anode and cathode through the second electrolyte solution for a second time period.

Some embodiments include the method of forming a metal oxide nanostructure of any one or more of the preceding embodiments, further comprising providing an anode comprising nickel and titanium and alloys thereof and at least one cathode.

In some embodiments, a method of preparing a biocompatible surface is provided, the method comprising placing an anode and at least one cathode in electrical contact through a first electrolyte solution comprising an organic solvent, a fluoride-bearing species, and water, applying a first voltage across the anode and cathode through the first electrolyte solution for a first time period, removing a portion of the anode surface, applying a second voltage across the anode and cathode through an electrolyte solution for a second time period.

Some embodiments include the method of preparing a biocompatible surface of any one or more of the preceding embodiments, further comprising providing an anode comprising nickel and titanium and alloys thereof and at least one cathode.

In some embodiments, a method of modifying the surface of an article is provided, the method comprising anodizing at least a portion of a surface of an article in a first electrolyte solution, wherein the first electrolyte solution does not contain an acid, and anodizing the portion of the surface of the stent in a second electrolyte solution, wherein the second electrolyte solution contains an acid.

Some embodiments include the method of modifying the surface of an article of any one or more of the preceding embodiments, wherein the article is anodized in the first electrolyte solution for about 5 minutes at about 25 V.

Some embodiments include the method of modifying the surface of an article of any one or more of the preceding embodiments, wherein the article is anodized in the second electrolyte solution for about 5 minutes at about 25 V.

Some embodiments include the method of modifying the surface of an article of any one or more of the preceding embodiments, wherein the article comprises nickel and titanium.

Some embodiments include the method of modifying the surface of an article of any one or more of the preceding embodiments, wherein the article is an implantable medical device.

Some embodiments include the method of modifying the surface of an article of any one or more of the preceding embodiments, wherein the article is a stent.

Some embodiments include the method of modifying the surface of an article of any one or more of the preceding embodiments, wherein the acid in the second electrolyte is hydroiodic acid.

Some embodiments include the method of modifying the surface of an article of any one or more of the preceding embodiments, wherein the acid in the second electrolyte is sulfuric acid.

Some embodiments include the method of modifying the surface of an article of any one or more of the preceding claims, wherein the acid in the second electrolyte is lactic acid.

Some embodiments include the method of modifying the surface of an article of any one or more of the preceding claims, wherein the acid in the second electrolyte is citric acid.

Any combination of methods, devices, systems, and features disclosed above are within the scope of this disclosure.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

In this disclosure, the indefinite article "a" and phrases "one or more" and "at least one" are synonymous and mean "at least one".

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

While certain embodiments of the invention have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Of course, the foregoing description is that of certain features, aspects and advantages of the present invention, to which various changes and modifications can be made without departing from the spirit and scope of the present invention. Moreover, the devices described herein need not feature all of the objects, advantages, features and aspects discussed above. Thus, for example, those of skill in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed devices.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. A method of forming a metal oxide nanostructure on a substrate, comprising:
    placing an anode comprising the substrate and placing at least one cathode in electrical contact through a first electrolyte, wherein the first electrolyte comprises an organic solvent, a fluoride-bearing species, and water;
    applying a first voltage across the anode and the at least one cathode through the first electrolyte for a first time period;
    modifying the first electrolyte or replacing the first electrolyte with another electrolyte to provide a second electrolyte;
    applying a second voltage across the anode and the at least one cathode through the second electrolyte for a second time period; and
    thereby forming the metal oxide nanostructure on the substrate;
    wherein the first electrolyte is modified by lowering the pH of the first electrolyte or increasing the acid concentration of the first electrolyte.

2. The method of forming a metal oxide nanostructure on a substrate of claim 1, wherein the second electrolyte comprises an organic solvent, a fluoride-bearing species, water and an acid.

3. The method of forming a metal oxide nanostructure on a substrate of claim 1, wherein the method further comprises removing a portion of surface of the anode after applying a first voltage across the anode and the at least one cathode through the first electrolyte for the first time period.

4. The method of forming a metal oxide nanostructure on a substrate of claim 1, wherein the method further comprises removing a portion of surface of the anode after applying a first voltage across the anode and the at least one cathode through the first electrolyte for the first time period; and wherein the portion of the anode surface is removed by etching, electrochemical anodization, ultrasonic cleaning, plasma cleaning, rinsing the anode surface by using a liquid, annealing, or a combination of such removal methods.

5. The method of forming a metal oxide nanostructure on a substrate of claim 1, wherein the substrate comprises nickel, titanium, or an alloy thereof.

6. The method of forming a metal oxide nanostructure on a substrate of claim 1, wherein the first electrolyte does not contain an acid; and wherein the second electrolyte contains an acid.

7. The method of forming a metal oxide nanostructure on a substrate of claim 1, wherein the first electrolyte does not contain an acid; and wherein the second electrolyte contains an acid, and wherein the acid in the second electrolyte is hydroiodic acid, sulfuric acid, lactic acid, phosphoric acid, citric acid, or a mixture thereof.

8. The method of forming a metal oxide nanostructure on a substrate of claim 1, wherein the fluoride bearing species is ammonium fluoride, ammonium bifluoride, potassium fluoride, sodium fluoride, calcium fluoride, magnesium fluoride, alkylated ammonium fluoride, or a mixture thereof.

9. The method of forming a metal oxide nanostructure on a substrate of claim 1, wherein the first time period and the second time period each are in a range of 1 minute to 30 minutes.

10. The method of forming a metal oxide nanostructure on a substrate of claim 1, wherein the first voltage is in a range of 10 V to 60 V.

11. The method of forming a metal oxide nanostructure on a substrate of claim 1, wherein the second voltage is in a range of 10 V to 60 V.

12. The method of forming a metal oxide nanostructure on a substrate of claim 1, wherein the substrate is anodized in the first electrolyte for about 5 minutes at about 25 V, and/or wherein the substrate is anodized in the second electrolyte for about 5 minutes at about 25 V.

13. The method of forming a metal oxide nanostructure on a substrate of claim 1, wherein:
    the first electrolyte does not contain an acid;
    the second electrolyte contains an acid;
    the acid in the second electrolyte is hydroiodic acid, sulfuric acid, lactic acid, phosphoric acid, citric acid, or a mixture thereof;
    the fluoride bearing species is ammonium fluoride, ammonium bifluoride, potassium fluoride, sodium fluoride, calcium fluoride, magnesium fluoride, alkylated ammonium fluoride, or a mixture thereof;
    the first time period and the second time period each are in a range of 1 minute to 30 minutes;
    the first voltage is in a range of 10 V to 60 V; and
    the second voltage is in a range of 10 V to 60 V.

14. The method of forming a metal oxide nanostructure on a substrate of claim 13, wherein the method further comprises removing a portion of the anode surface after applying a first voltage across the anode and the at least one cathode through the first electrolyte for the first time period.

* * * * *